US 10,588,603 B2

(12) United States Patent
Yang et al.

(10) Patent No.: US 10,588,603 B2
(45) Date of Patent: Mar. 17, 2020

(54) ULTRASOUND APPARATUS AND INFORMATION PROVIDING METHOD OF THE ULTRASOUND APPARATUS

(71) Applicants: SAMSUNG ELECTRONICS CO., LTD., Suwon-si (KR); SAMSUNG MEDISON CO., LTD., Hongcheon-gun (KR)

(72) Inventors: Eun-ho Yang, Seoul (KR); Hyoung-jin Kim, Hongcheon-gun (KR); Jin-young Choi, Chuncheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/753,519

(22) Filed: Jun. 29, 2015

(65) Prior Publication Data

US 2015/0297186 A1 Oct. 22, 2015

Related U.S. Application Data

(63) Continuation of application No. 14/035,589, filed on Sep. 24, 2013.

(30) Foreign Application Priority Data

Sep. 24, 2012 (KR) .................. 10-2012-0105959
Mar. 13, 2013 (KR) .................. 10-2013-0026809

(51) Int. Cl.
*A61B 8/00* (2006.01)
*A61B 8/08* (2006.01)
(Continued)

(52) U.S. Cl.
CPC .............. *A61B 8/465* (2013.01); *A61B 8/14* (2013.01); *A61B 8/4444* (2013.01); *A61B 8/463* (2013.01);
(Continued)

(58) Field of Classification Search
None
See application file for complete search history.

(56) References Cited

U.S. PATENT DOCUMENTS 4,574,635 A 3/1986 't Hoen
5,315,999 A 5/1994 Kinicki et al.
(Continued)

FOREIGN PATENT DOCUMENTS

CN 1771009 A 5/2006
CN 101163986 A 4/2008
(Continued)

OTHER PUBLICATIONS

Communication dated Nov. 26, 2014 issued by the Korean Intellectual Property Office in counterpart Korean Application No. 10-2013-0026809.
(Continued)

*Primary Examiner* — Carolyn A Pehlke
*Assistant Examiner* — Marjan Saboktakin
(74) *Attorney, Agent, or Firm* — Staas & Halsey LLP

(57) ABSTRACT

An information providing method which is implementable by using an ultrasound apparatus includes obtaining ultrasound image data which relates to an object; displaying, on a first area of a screen, a gain setup window for setting a gain of the obtained ultrasound image data; receiving a gain which is set by a user on the gain setup window; and displaying, on a second area of the screen, an ultrasound image of the object to which the set gain is applied.

9 Claims, 21 Drawing Sheets

(51) Int. Cl.
*A61B 8/14* (2006.01)
*G01S 7/52* (2006.01)
*G06F 3/0482* (2013.01)
*G06F 3/0484* (2013.01)
*G06F 3/0488* (2013.01)

(52) U.S. Cl.
CPC .............. *A61B 8/467* (2013.01); *A61B 8/523* (2013.01); *A61B 8/5207* (2013.01); *A61B 8/5223* (2013.01); *A61B 8/54* (2013.01); *G01S 7/52033* (2013.01); *G01S 7/52074* (2013.01); *G06F 3/0482* (2013.01); *G06F 3/0488* (2013.01); *G06F 3/04842* (2013.01); *G06F 3/04847* (2013.01); *A61B 8/4438* (2013.01); *A61B 8/464* (2013.01); *A61B 8/469* (2013.01); *A61B 8/565* (2013.01); *G01S 7/52084* (2013.01); *G01S 7/52098* (2013.01)

(56) References Cited

U.S. PATENT DOCUMENTS

| | | | |
|---|---|---|---|
| 5,482,045 A | 1/1996 | Rust et al. | |
| 6,063,030 A | 5/2000 | Vara et al. | |
| 6,468,212 B1 * | 10/2002 | Scott | A61B 8/00 600/437 |
| 9,402,601 B1 | 8/2016 | Berger et al. | |
| 2003/0187353 A1 | 10/2003 | Ng | |
| 2004/0015079 A1 * | 1/2004 | Berger | A61B 8/461 600/437 |
| 2004/0168115 A1 | 8/2004 | Bauernshmidt et al. | |
| 2005/0059892 A1 | 3/2005 | Dubois et al. | |
| 2005/0222871 A1 * | 10/2005 | Motoki | G06F 19/321 705/2 |
| 2007/0066894 A1 | 3/2007 | Bartol et al. | |
| 2007/0230907 A1 | 10/2007 | Takao | |
| 2007/0232907 A1 | 10/2007 | Pelissier et al. | |
| 2008/0112265 A1 | 5/2008 | Urbano et al. | |
| 2008/0161688 A1 | 7/2008 | Poland | |
| 2008/0208045 A1 | 8/2008 | Rielly | |
| 2009/0043195 A1 | 2/2009 | Poland | |
| 2009/0069682 A1 | 3/2009 | Hastings et al. | |
| 2010/0049046 A1 | 2/2010 | Peiffer et al. | |
| 2010/0049050 A1 | 2/2010 | Pelissier et al. | |
| 2010/0064257 A1 | 3/2010 | Buck et al. | |
| 2010/0145195 A1 | 6/2010 | Hyun | |
| 2011/0043434 A1 * | 2/2011 | Roncalez | G06F 3/04847 345/3.1 |
| 2011/0112399 A1 | 5/2011 | Willems et al. | |
| 2011/0246943 A1 | 10/2011 | Fujibayashi | |
| 2012/0232393 A1 | 9/2012 | Lee et al. | |
| 2013/0144169 A1 | 6/2013 | Lee et al. | |
| 2013/0249842 A1 | 9/2013 | Varna | |
| 2014/0109006 A1 | 4/2014 | Yoo | |
| 2014/0143690 A1 | 5/2014 | Roncalez et al. | |
| 2015/0150521 A2 | 6/2015 | Roncalez et al. | |

FOREIGN PATENT DOCUMENTS

| | | | |
|---|---|---|---|
| CN | 101040245 A | 9/2008 | |
| CN | 101438966 A | 5/2009 | |
| CN | 101474078 A | 7/2009 | |
| CN | 101959463 A | 1/2011 | |
| CN | 101987023 A | 3/2011 | |
| CN | 102178548 A | 9/2011 | |
| EP | 1 929 952 A1 | 6/2008 | |
| JP | 7-318989 | 12/1995 | |
| JP | 10-248843 A | 9/1998 | |
| JP | 3621489 | 11/2004 | |
| JP | 3824107 | 7/2006 | |
| JP | 2006-296978 A | 11/2006 | |
| JP | 4220892 | 2/2009 | |
| JP | 2009-178277 A | 8/2009 | |
| JP | 2010517439 A | 5/2010 | |
| KR | 10-2006-0033845 A | 4/2006 | |
| KR | 10-2007-0032140 A | 3/2007 | |
| KR | 10-2008-0051917 A | 6/2008 | |
| KR | 10-2010-0128290 A | 12/2010 | |
| WO | WO 2009109585 A1 * | 9/2009 | .............. A61B 8/00 |
| WO | 2010/051587 A1 | 5/2010 | |
| WO | WO 2011/133917 A2 | 10/2011 | |
| WO | 2012077876 A1 | 6/2012 | |

OTHER PUBLICATIONS

Communication, dated Jan. 31, 2014, issued by the European Patent Office in counterpart European Patent Application No. 13185807.8.
International Search Report (PCT/ISA/210), dated Jan. 16, 2014, issued by the International Searching Authority in counterpart International Patent Application No. PCT/KR2013/008503.
Written Opinion (PCT/ISA/237), dated Jan. 16, 2014, issued by the International Searching Authority in counterpart International Patent Application No. PCT/KR2013/008503.
Communication dated Dec. 23, 2015 issued by the Korean Intellectual Property Office in counterpart Korean Patent Application No. 10-2013-0026809.
Communication dated Jan. 18, 2016 issued by the Korean Intellectual Property Office in counterpart Korean Patent Application No. 10-2015-0087583.
Communication dated Nov. 10, 2015 issued by the European Patent Office in counterpart European Patent Application No. 15183958.6.
Communication dated Jul. 10, 2015 issued by the Korean Intellectual Property Office in counterpart Korean Application No. 10-2015-0087583.
Communication dated Aug. 6, 2015, issued by the State Intellectual Property Office of the People's Republic of China in counterpart Chinese Application No. 201310438897.1.
Communication dated Sep. 17, 2015, issued by the Korean Intellectual Property Office in counterpart Korean Application No. 10-2015-0107417.
Communication from the Korean Intellectual Property Office dated Apr. 22, 2016 in a counterpart Korean application No. 10-2015-0087583.
Communication from the Korean Intellectual Property Office dated May 31, 2016 in a counterpart Korean application No. 10-2013-0026809.
Communication from the State Intellectual Property Office of P.R. China dated May 6, 2016 in a counterpart Chinese application No. 201310438897.1.
Communication from the European Patent Office dated Apr. 20, 2016 in a counterpart European Application No. 13185807.8.
Communication from the European Patent Office dated May 3, 2016 in a counterpart European Application No. 13185807.8.
Communication from the European Patent Office dated Apr. 28, 2016 in a counterpart European Application No. 15151487.4.
Communication dated Dec. 13, 2016, issued by the European Patent Office in counterpart European Application No. 15151487.4.
Office Action issued in U.S. Appl. No. 14/035,589 dated Sep. 11, 2015.
Office Action issued in U.S. Appl. No. 14/035,589 dated Dec. 31, 2015.
Office Action issued in U.S. Appl. No. 14/035,589 dated Apr. 21, 2016.
Office Action issued in U.S. Appl. No. 14/035,589 dated Aug. 25, 2016.
Advisory Action issued in U.S. Appl. No. 14/035,589 dated Dec. 1, 2016.
Office Action issued in U.S. Appl. No. 14/530,113 dated Apr. 20, 2017.
Office Action issued in U.S. Appl. No. 14/528,331 dated Sep. 23, 2015.
Office Action issued in U.S. Appl. No. 14/528,331 dated Mar. 25, 2016.
Office Action issued in U.S. Appl. No. 14/528,331 dated Jun. 30, 2016.
Office Action issued in U.S. Appl. No. 14/528,331 dated Dec. 30, 2016.

(56) References Cited

OTHER PUBLICATIONS

Advisory Action issued in U.S. Appl. No. 14/528,331 dated May 1, 2017.
Office Action issued in U.S. Appl. No. 14/667,274 dated Aug. 28, 2015.
Office Action issued in U.S. Appl. No. 14/667,274 dated Dec. 31, 2015.
Office Action issued in U.S. Appl. No. 14/667,274 dated Apr. 19, 2016.
Office Action issued in U.S. Appl. No. 14/667,274 dated Aug. 11, 2016.
Office Action issued in U.S. Appl. No. 14/836,367 dated Apr. 18, 2016.
Office Action issued in U.S. Appl. No. 14/836,367 dated Aug. 11, 2016.
Advisory Action issued in U.S. Appl. No. 14/836,367 dated Nov. 30, 2016.
Office Action issued in U.S. Appl. No. 14/836,367 dated Jun. 21, 2017.
U.S. Appl. No. 14/035,589, filed Sep. 24, 2013, Eun-ho Yang et al., Samsung Electronics Co., Ltd.
U.S. Appl. No. 14/528,331, filed Oct. 30, 2014, Eun-ho Yang et al., Samsung Electronics Co., Ltd.
U.S. Appl. No. 14/667,274, filed Mar. 24, 2015, Eun-ho Yang et al., Samsung Electronics Co., Ltd.
U.S. Appl. No. 14/836,367, filed Aug. 26, 2015, Eun-ho Yang et al., Samsung Electronics Co., Ltd.
U.S. Appl. No. 14/530,113, filed Oct. 31, 2014, Eun-ho Yang et al., Samsung Electronics Co., Ltd.
Office Action dated Mar. 5, 2018, in U.S. Appl. No. 14/035,589.
Office Action dated Mar. 26, 2018, in U.S. Appl. No. 14/836,367.
Office Action issued in U.S. Appl. No. 14/667,274 dated Oct. 31, 2017.
Extended European Search Report dated Oct. 12, 2017, in corresponding European Patent Application No. 15854572.3.
Office Action dated Jan. 12, 2018, in U.S. Appl. No. 14/530,113.
Office Action dated Feb. 6, 2019 in U.S. Appl. No. 14/530,113.
Office Action dated Feb. 6, 2019 in U.S. Appl. No. 14/035,589.
Office Action dated Dec. 26, 2018 in U.S. Appl. No. 14/528,331.
Office Action dated Jun. 14, 2018, in U.S. Appl. No. 14/667,274.
Office Action dated May 30, 2018, in U.S. Appl. No. 14/528,331.
"SonixTOUCH Ultrasound System User Manual", Ultrasonix Medical Corporation, 00.040.216, Revision C, Mar. 16, 2009.
"Sonix Series Ultrasound System Service Manual", Ultrasonix Medical Corporation, SSM-001, Revision F, Aug. 17, 2006.
Korean Office Action dated Oct. 30, 2018 in Korean Patent Application No. 10-2017-7014664.
Office Action dated Oct. 16, 2018, in U.S. Appl. No. 14/035,589.
Korean Office Action dated Feb. 28, 2019, in Korean Patent Application No. 10-2017-7014664.
European Search Report dated Jan. 25, 2019, in European Patent Application No. 18195810.9.
Final Office Action dated May 17, 2019 in co-pending U.S. Appl. No. 14/530,113.
Notice of Allowance dated Sep. 6, 2019 in co-pending U.S. Appl. No. 14/667,274.
Notice of Allowance dated Sep. 6, 2019 in co-pending U.S. Appl. No. 14/836,367.
Chinese Patent Office Action issued in Chinese Patent Application No. 201610196001.7 dated May 20, 2019.
Extended European Search Report issued in corresponding European Patent Application No. 18000846.8 dated Jun. 14, 2019.
Chinese Patent Office Action issued in Chinese Patent Application No. 201580071438.1 dated Jun. 28, 2019.
European Search Report issued in corresponding European Patent Application No. 18000847.6 dated Jun. 13, 2019.
Chinese Patent Office Action dated Sep. 24, 2019 in Chinse Patent Application No. 201710512639.1.
Notice of Allowance dated Nov. 20, 2019 in co-pending U.S. Appl. No. 14/530,113.
Chinse Office Action issued in Chinese Patent Application No. 201710513696.1 dated Jan. 21, 2020.

\* cited by examiner

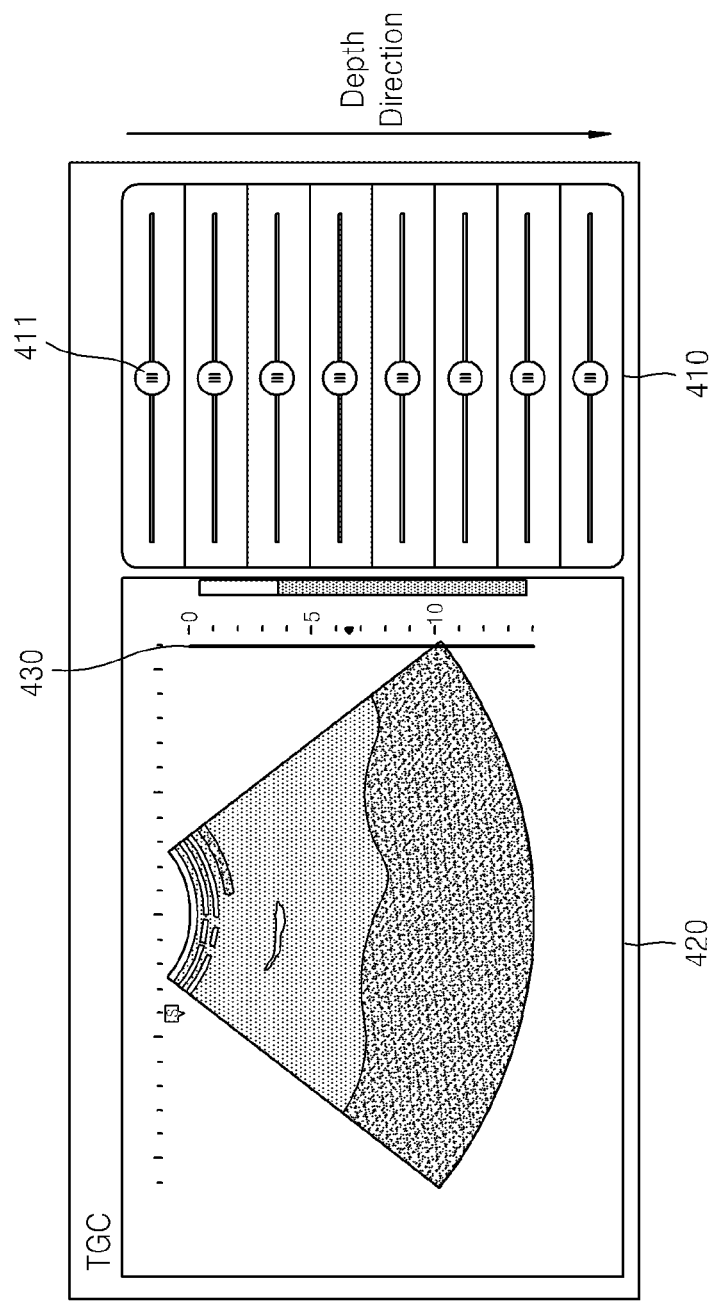

FIG. 13

| | |
|---|---|
| Frequency | —1305 |
| Dynamic Range | —1310 |
| Frame Average | —1315 |
| Reject Level | —1320 |
| Gray Map | —1325 |
| Spatial Compound | —1330 |
| DMR+ | —1335 |
| Harmonic | —1340 |
| Scan Area | —1345 |
| Edge Enhance | —1350 |
| Speed | —1355 |
| Power | —1360 |
| Line Density | —1365 |
| FSI | —1370 |
| Focus Number | —1375 |
| Gain | —1380 |
| Depth | —1385 |

ULTRASOUND APPARATUS AND INFORMATION PROVIDING METHOD OF THE ULTRASOUND APPARATUS

CROSS-REFERENCE TO RELATED PATENT APPLICATIONS

This is a continuation of application Ser. No. 14/035,589 filed Sep. 24, 2013, which claims priority from Korean Patent Application No. 10-2012-0105959, filed on Sep. 24, 2012, in the Korean Intellectual Property Office, and priority from Korean Patent Application No. 10-2013-0026809, filed on Mar. 13, 2013, in the Korean Intellectual Property Office, the disclosures of which are incorporated herein by reference in their respective entireties.

BACKGROUND

1. Technical Field

Exemplary embodiments relate to an ultrasound apparatus for providing a gain setup window for setting a gain or a list of one or more preset gains, and an information providing method which is implementable by using the ultrasound apparatus.

2. Description of the Related Art

An ultrasound diagnosis apparatus obtains an image of soft tissues or blood flow by transmitting an ultrasound signal from a body surface of an object toward a predetermined site inside the body, and receiving an ultrasound signal reflected from tissues in the body.

The ultrasound diagnosis apparatus is small, is inexpensive, and allows real time display. Further, because it does not cause an exposure to radiation and thus is safe, the ultrasound diagnosis apparatus is broadly used together with other imaging diagnosis apparatuses, such as an X-ray diagnostic apparatus, a computerized tomography (CT) scanner, a magnetic resonance image (MRI) apparatus, and a nuclear medicine diagnostic apparatus.

In general, an ultrasonic beam that propagates through tissues is reduced in amplitude or intensity as a function of a transmission distance. Attenuation occurs in a form that the amplitude reduces greatly if the transmission distance is large. Due to the attenuation, the intensity of a received echo ultrasound signal may not be uniform. In particular, an ultrasound image which is based on the echo ultrasound signal may not have a uniform brightness or may partially have a poor quality. Accordingly, a system for allowing a user to easily compensate the sensitivity of an ultrasound image is required.

SUMMARY

Exemplary embodiments provide an ultrasound apparatus for providing on a touchscreen a user interface for adjusting a gain and a list of one or more gains previously set by a user, and an information providing method which is implementable by using the ultrasound apparatus.

Exemplary embodiments also provide an ultrasound apparatus for applying to ultrasound image data a preset gain which corresponds to identification information which relates to a probe connected to the ultrasound apparatus, and an information providing method which is implementable by using the ultrasound apparatus.

According to an aspect of one or more exemplary embodiments, there is provided an information providing method which is executable by using an ultrasound apparatus, the method including obtaining ultrasound image data which relates to an object; displaying, on a first area of a screen, a gain setup window which relates to setting a gain with respect to the obtained ultrasound image data; receiving a gain which is set by a user on the gain setup window; and displaying, on a second area of the screen, an ultrasound image of the object to which the set gain is applied.

The gain may include at least one from among a time gain compensation (TGC) value and a lateral gain compensation (LGC) value.

The screen may include a touch screen.

The method may further include displaying an initial gain based on a depth of the object, on the gain setup window; and displaying, on the second area of the screen, an ultrasound image to which the initial gain is applicable.

The method may further include displaying at least one slide bar which relates to setting a gain, on the gain setup window.

The method may further include aligning and displaying the at least one slide bar along a depth direction of the ultrasound image.

The method may further include sensing a touch input of the user on the at least one slide bar; and extracting a gain which corresponds to a position of the sensed touch input.

The method may further include sensing a drag input of the user which is provided in a direction which is perpendicular to the at least one slide bar on the gain setup window; and extracting a gain which corresponds to a depth of the ultrasound image based on a position of the drag input.

The method may further include moving and displaying an adjustment button on the at least one slide bar based on the extracted gain.

The method may further include obtaining a gain line which corresponds to the gain which is set on the gain setup window; and displaying the obtained gain line on the second area of the screen.

The method may further include displaying a list of at least one preset gain on a third area of the screen.

The method may further include receiving a selection of one preset gain from among the at least one preset gain included in the displayed list; displaying the selected preset gain on the gain setup window; and displaying, on the second area of the screen, an ultrasound image to which the selected preset gain is applicable.

The method may further include receiving an additional setup from the user in relation to the selected preset gain.

The method may further include storing the gain which is set on the gain setup window based on a user input; and displaying an image of the stored gain on the third area of the screen.

The method may further include further displaying at least one from among a body marker, application information, and probe setup information on the displayed list.

The method may further include storing, in an external storage medium, the gain which is set on the gain setup window.

The method may further include mapping and storing the gain which is set on the gain setup window and at least one parameter which relates to the ultrasound image.

The parameter may include at least one from among a frequency, a dynamic range, a frame average, a reject level, a gray map, a spatial compound, a dynamic magnetic resonance (DMR+), a harmonic, a scan area, an edge enhance, a speed, a power, a line density, a full spectrum image (FSI), a focus number, and a depth.

The method may further include transmitting the gain which is set on the gain setup window to an external apparatus via at least one from among a wired communication and a wireless communication.

According to another aspect of one or more exemplary embodiments, there is provided an ultrasound apparatus which includes: an obtaining unit which is configured to obtain ultrasound image data which relates to an object; a display unit which is configured to display, on a first area of a screen, a gain setup window which relates to setting a gain with respect to the obtained ultrasound image data, and to display an ultrasound image of the object on a second area of the screen; a user input unit which is configured to receive a gain which is set by a user on the gain setup window; an image processor which is configured to generate the ultrasound image to be displayed on the second area of the screen by applying, to the ultrasound image data, the gain which is set on the gain setup window; and a controller which is configured to control the obtaining unit, the display unit, the user input unit, and the image processor.

The display unit of the ultrasound apparatus may be further configured to display at least one slide bar which relates to setting a gain, on the gain setup window.

The controller of the ultrasound apparatus may be further configured to control the display unit to obtain a gain line which corresponds to the gain which is set on the gain setup window and to display the obtained gain line on the second area of the screen.

The display unit of the ultrasound apparatus may be further configured to display a list of at least one preset gain on a third area of the screen.

The ultrasound apparatus may further include a memory which is configured to store the gain which is set on the gain setup window.

According to another aspect of one or more exemplary embodiments, there is provided an information providing method which is implementable by using an ultrasound apparatus, the method including displaying a list of preset gains on a screen; receiving a selection of one preset gain from among the preset gains included in the displayed list; and applying the selected preset gain to ultrasound image data which relates to an object.

According to another aspect of one or more exemplary embodiments, there is provided an information providing method which is executable by using an ultrasound apparatus, the method including obtaining ultrasound image data which relates to an object; displaying, on a first area of a screen, a gain setup window which relates to setting a gain with respect to the obtained ultrasound image data; displaying an ultrasound image of the object on a second area of the screen based on the obtained ultrasound image data; and displaying a list of preset gains on a third area of the screen.

The method may further include obtaining the list of the preset gains from an external storage medium.

The method may further include receiving a selection of one preset gain from among the preset gains included in the displayed list; displaying the selected preset gain on the gain setup window; and displaying, on the second area of the screen, an ultrasound image to which the selected preset gain is applicable. The method may further include receiving an additional setup from a user in relation to the preset gain which is displayed on the gain setup window.

The method may further include storing the additionally set gain.

The method may further include storing the additionally set gain in the external storage medium.

The method may further include displaying at least one parameter which is mapped to the selected preset gain, and the parameter may include a preset value which relates to the ultrasound image.

The method may further include determining at least one parameter which is mapped to the selected preset gain; and applying the determined at least one parameter to a system of the ultrasound apparatus.

The method may further include displaying at least one from among a list of gray maps which list relates to determining a gray scale and a list of curves which list relates to selecting a predetermined area of 3-dimensional (3D) volume data, on a fourth area of the screen.

According to another aspect of one or more exemplary embodiments, there is provided an information providing method which is executable by using an ultrasound apparatus, the method including determining identification information which relates to a probe which is connected to the ultrasound apparatus; extracting a preset gain which corresponds to the determined identification information which relates to the probe; and applying the extracted preset gain to ultrasound image data.

The method may further include displaying a probe list which includes identification information which relates to at least one probe which is connected to the ultrasound apparatus; receiving a selection of one probe from among the at least one probe for which a corresponding identification information is included in the displayed probe list; and applying, to the ultrasound image data, a preset gain which corresponds to the identification information which corresponds to the selected probe.

The method may further include extracting a plurality of preset gains which respectively correspond to the determined identification information which relates to the probe; displaying a list of the extracted plurality of the preset gains; and receiving a selection of one preset gain from among the plurality of the preset gains which are displayed on the list.

The method may further include receiving application information which represents a diagnosis department; and extracting a preset gain which corresponds to both of the determined identification information which relates to the probe and the received application information.

The method may further include displaying the extracted preset gain on a predetermined area of a screen.

The method may further include receiving an additional setup from a user in relation to the displayed preset gain.

The method may further include displaying, on a screen, a gain setup window which relates to setting a gain with respect to ultrasound image data; receiving a gain which is set by a user on the gain setup window; and mapping and storing the set gain and the determined identification information which relates to the probe.

The method may further include displaying, on a screen, a gain setup window which relates to setting a gain with respect to ultrasound image data; receiving a gain which is set by a user on the gain setup window; and mapping and storing the set gain, the determined identification information which relates to the probe, and application information which represents a diagnosis department.

BRIEF DESCRIPTION OF THE DRAWINGS

The above and other features and advantages of the present inventive concept will become more apparent by describing in detail exemplary embodiments thereof with reference to the attached drawings in which:

FIG. 4 is an image of a gain setup window for setting a gain, according to an exemplary embodiment;

FIG. 13 is a table which includes setup parameters which relate to an ultrasound image, according to an exemplary embodiment;

DETAILED DESCRIPTION

Figure 1A:
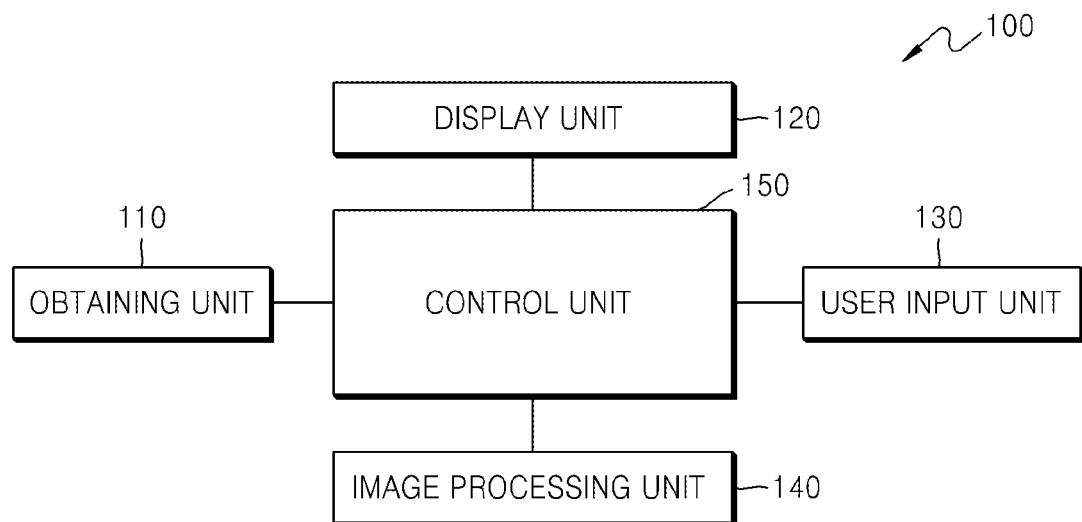
FIGS. 1A, 1B, and 1C are diagrams which illustrate an ultrasound apparatus, according to an exemplary embodiment.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. In addition, some terms may be arbitrarily selected by the applicant, and in this case, the meaning of the selected terms will be described in detail in the detailed description. Thus, the terms used herein should be defined based on the meaning of the terms together with the description throughout the specification.

Further, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

Throughout the specification, "an ultrasound image" refers to an image which is obtained from an object by using ultrasonic waves. The object may refer to a part of the body. For example, the object may include an organ such as any one or more of a liver, a heart, a uterus, a brain, a breast, or an abdomen, or a fetus.

The ultrasound image may be obtained via any one or more of various modalities. For example, the ultrasound image may include at least one of a brightness mode (B mode) image, a color mode (C mode) image, and a Doppler mode (D mode) image. Further, according to an exemplary embodiment, the ultrasound image may include a 2-dimensional (2D) image or a 3-dimensional (3D) image.

Throughout the specification, "a user" may be, but is not limited to, a medical expert such as a doctor, a nurse, a medical technologist, or a medical imaging specialist.

Hereinafter, the present inventive concept will be described in detail by explaining exemplary embodiments thereof with reference to the attached drawings. The present inventive concept may, however, be embodied in many different forms and should not be construed as being limited to the exemplary embodiments set forth herein; rather, these exemplary embodiments are provided so that this disclosure will be thorough and complete, and will fully convey the present inventive concept to one of ordinary skill in the art. In the drawings, the thicknesses of layers and regions are exaggerated for clarity, and like reference numerals denote like elements.

As used herein, the term "and/or" includes any and all combinations of one or more of the associated listed items. Expressions such as "at least one of," when preceding a list of elements, modify the entire list of elements and do not modify the individual elements of the list.

Figure 1B:
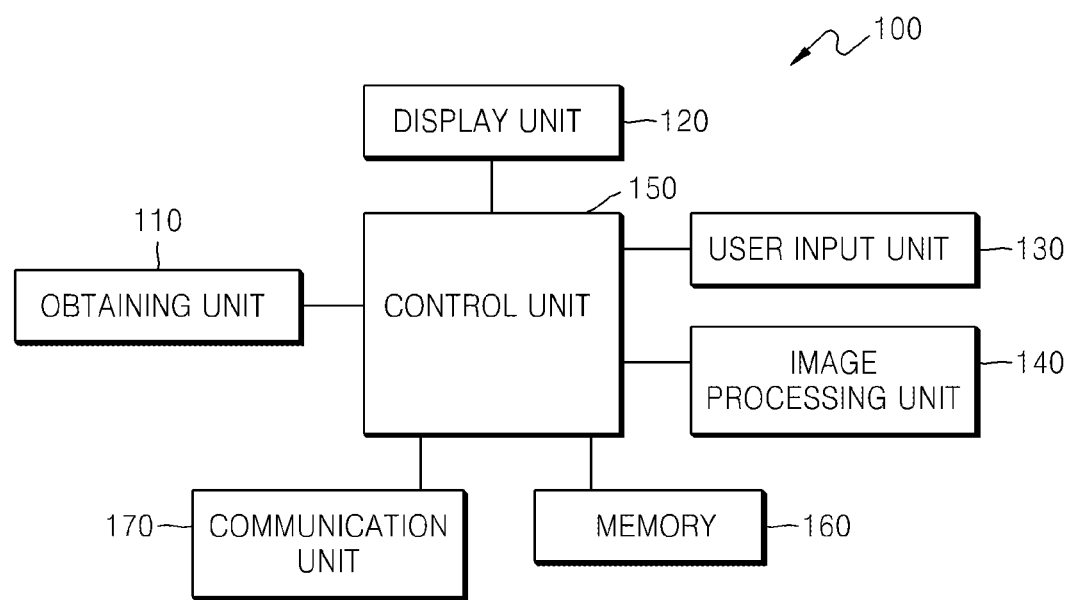
Figure 1C:
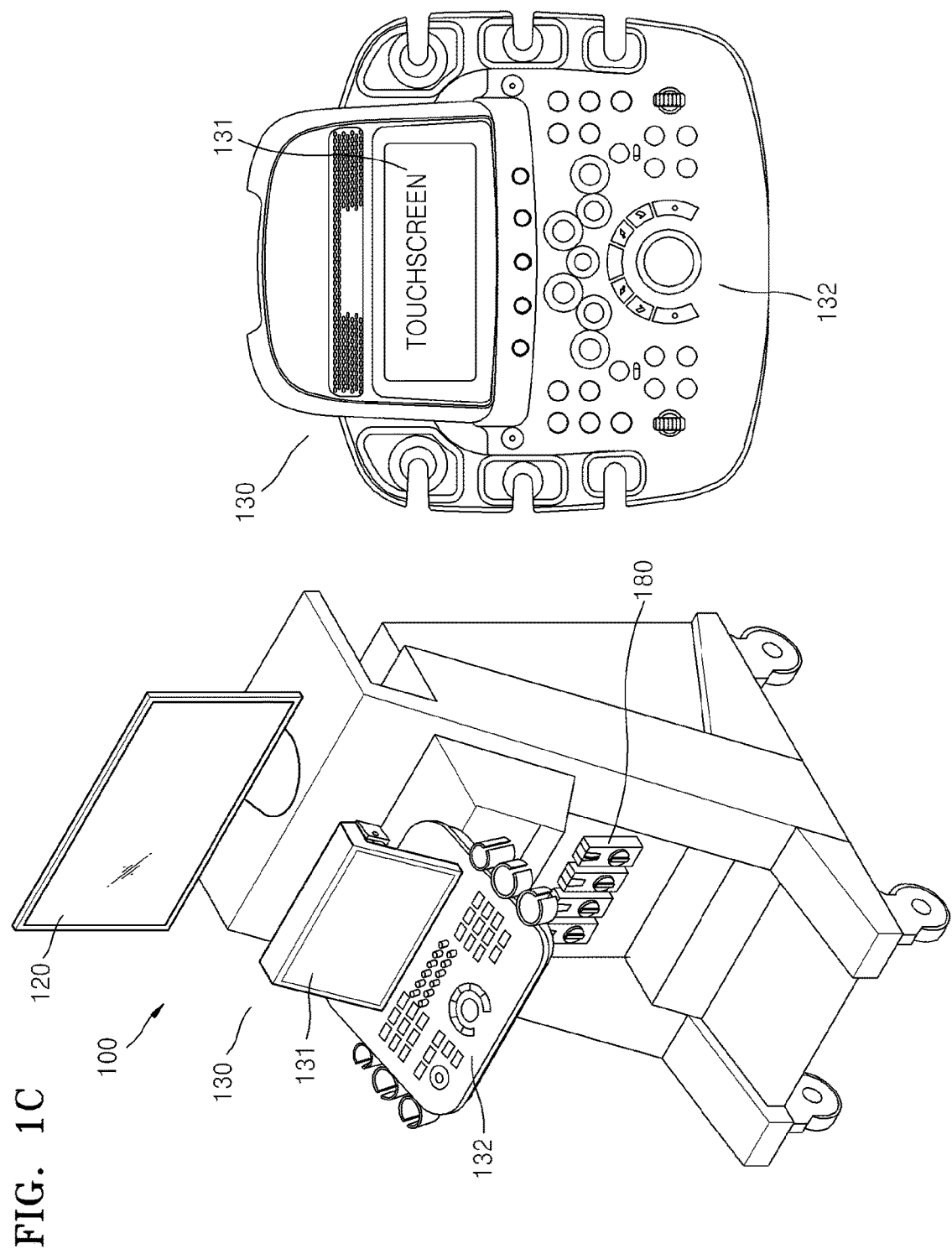

FIGS. 1A, 1B, and 1C are diagrams which illustrate an ultrasound apparatus 100, according to an exemplary embodiment.

The ultrasound apparatus 100 refers to a device for obtaining an ultrasound image data from an object by using ultrasonic waves and providing, to a user, a graphic user interface (GUI) for setting a gain of the ultrasound image data.

The ultrasound apparatus 100 may be formed in various forms. For example, the ultrasound apparatus 100 described in this specification may be formed as a mobile device and/or as a stationary device. Examples of the mobile device which may be used for such an ultrasound apparatus 100 include a laptop computer, a personal digital assistant (PDA), and a tablet personal computer (PC).

As illustrated in FIG. 1A, the ultrasound apparatus 100 may include an obtaining unit 110, a display unit 120 (also referred to herein as a display 120), a user input unit 130, an image processing unit 140 (also referred to herein as an image processor 140), and a control unit 150 (also referred to herein as a controller 150). However, not all of the elements illustrated in FIG. 1A are essential. The ultrasound apparatus 100 may include the illustrated elements and other elements, or may include only some of the illustrated elements.

The elements of the ultrasound apparatus 100 will now be described individually, i.e., on a one-by-one basis.

The obtaining unit 110 may obtain ultrasound image data which relates to an object. The ultrasound image data may include 2-dimensional (2D) ultrasound image data or 3-dimensional (3D) ultrasound image data which relates to the object.

The obtaining unit 110 may include a probe (not shown) which is configured for transmitting and receiving an ultrasound signal, and a beam former (not shown) which is configured for focusing the transmitted or received ultrasound signal.

The probe may include at least one of a 1-dimensional (1D) probe, a 1.5-dimensional (1.5D) probe, a 2D (matrix) probe, and a 3D probe.

The display unit 120 may display information which is processed by the ultrasound apparatus 100. For example, the display unit 120 may display the ultrasound image of the object on a screen, or may display a user interface (UI) and/or a GUI which is related to a function setup.

If a display panel and a touchpad are layered to form a touchscreen, the display unit 120 may be used as an input device and/or as an output device. The display unit 120 may include at least one of a liquid crystal display, a thin film transistor-liquid crystal display, an organic light-emitting diode, a flexible display, a 3D display, and an electrophoretic display. In accordance with the form of the ultrasound apparatus 100, the ultrasound apparatus 100 may include two or more display units 120.

The user input unit 130 refers to an element which is configured for receiving, from a user, data which is usable for controlling the ultrasound apparatus 100. For example, the user input unit 130 may include, but is not limited to, any one or more of a keypad, a dome switch, a touchpad (a contact capacitance type, a pressure resistive type, an infrared sensing type, a surface ultrasound transfer type, an integral tension measurement type, a piezo effect type, etc.), a jog wheel, and/or a jog switch. In particular, as described above, if a touchpad and a display panel are layered, the layered touchpad and the display panel may be referred to as a touchscreen.

A touchscreen may be configured to detect a proximity touch and/or a real touch. In this specification, a "real touch" refers to a case by which a pointer actually touches a screen, and a "proximity touch" refers to a case by which a pointer does not actually touch or make physical contact with a screen, but approaches the screen to within a predetermined distance. In this specification, a pointer refers to a tool which is configured for performing a real touch and/or a proximity touch on a certain portion of a displayed screen. Examples of the pointer include a stylus pen and a finger.

Although not shown in FIG. 1A, in order to sense a real touch or a proximity touch on a touchscreen, various sensors may be formed inside or near the touchscreen. An example of a sensor which is configured for sensing a touch on a touchscreen may include a haptic sensor. The haptic sensor refers to a sensor which is configured for sensing a touch on a certain object to a level which is equal to or higher than a corresponding sensory level of a person. The haptic sensor may sense various types of information such as, for example, a roughness on a contact surface, hardness of a contact object, and/or temperature at a contact point.

Also, an example of a sensor which is configured for sensing a touch on a touchscreen may include a proximity sensor. The proximity sensor refers to a sensor which is configured for detecting an object that approaches a predetermined detection surface, or detecting whether an object exists nearby, by using a force of an electromagnetic field or infrared light without requiring using a mechanical contact. Examples of the proximity sensor include a transmissive photoelectric sensor, a direct reflective photoelectric sensor, a mirror reflective photoelectric sensor, a high-frequency oscillation proximity sensor, a capacitive proximity sensor, a magnetic proximity sensor, and an infrared proximity sensor.

Touch gestures of a user may include any one or more of a tap, a touch and hold, a double tap, a drag, a panning, a flick, a drag and drop, a swipe, etc.

The image processing unit 140 may be configured apply a gain which is set by a user to the ultrasound image data. In particular, the image processing unit 140 may generate or change an ultrasound image which is displayed on a screen by applying a gain which is set by a user to the ultrasound image data.

The control unit 150 may typically control overall operations of the ultrasound apparatus 100. In particular, the control unit 150 may control overall operations of the obtaining unit 110, the display unit 120, the user input unit 130, and the image processing unit 140.

As illustrated in FIG. 1B, the ultrasound apparatus 100 may further include a memory 160 and a communication unit 170, in addition to the obtaining unit 110, the display unit 120, the user input unit 130, and the image processing unit 140.

The memory 160 may be configured to store programs which are configured for enabling the control unit 150 to process and control, and to store input and output data (e.g., a preset gain, an ultrasound image, testee information, probe information, application information, and a body marker).

The memory 160 may include at least one storage medium from among a flash memory, a hard disk, a micro multimedia card, a card-type memory (e.g., a security digital (SD) or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk. Also, the ultrasound apparatus 100 may operate a web storage and/or a cloud server for performing the storing function of the memory 160 on the Internet.

The ultrasound apparatus 100 may store a gain which is set on a gain setup window, in the memory 160 (e.g., an internal storage medium or an external storage medium).

The communication unit 170 may include at least one element for enabling communications between the ultrasound apparatus 100 and an external apparatus. For example, the communication unit 170 may include at least one of a short distance communication module, a mobile communication module, a wireless Internet module, a wired Internet module, etc.

The short distance communication module refers to a module which is configured for performing short distance communications. As a short distance communication technology, any one or more of Wireless Local Area Network (WLAN) (e.g., Wireless Fidelity (Wi-Fi)), BLUETOOTH wireless communication technology, BLUETOOTH Low Energy (BLE) wireless communication technology, Ultra Wideband (UWB), ZigBee, Near Field Communication (NFC), Wi-Fi Direct (WFD), Infrared Data Association (IrDA), etc. may be used.

The mobile communication module is configured to transmit and/or receive wireless signals to and from at least one of a base station, an external device, and a server, on a mobile communication network. The wireless Internet module refers to a module which is configured for establishing a wireless Internet connection and may be included in or separated from the ultrasound apparatus 100. The wired Internet module refers to a module which is configured for establishing a wired Internet connection.

The communication unit 170 may be configured transmit at least one preset gain to an external apparatus via wired and/or wireless communications. The external apparatus may be, but is not limited to, any one or more of a mobile phone, a smart phone, a laptop computer, a tablet PC, an electric book device, a digital broadcast device, a PDA, a portable multimedia player (PMP), and a digital camera.

FIG. 1C shows the external shape of the ultrasound apparatus 100.

As illustrated in FIG. 1C, the ultrasound apparatus 100 may include the display unit 120, the user input unit 130, and a probe connection unit 180.

The display unit 120 may be configured to display an ultrasound image of an object. For example, the display unit 120 may display any one or more of a brightness mode (B mode) image, a color mode (C mode) image, a Doppler mode (D mode) image, a 2D image, and/or a 3D image.

The user input unit 130 may include a touchscreen 131 and a control panel 132. The touchscreen 131 may be configured to display any one or more of an ultrasound image, a gain setup window, a list of preset gains, etc. Also, the touchscreen 131 may display a probe list which includes identification information which relates to probes which are connected to the ultrasound apparatus 100, a plurality of parameters which are set by a user, and a list of preset items which have previously been set by a system or a user.

The ultrasound image which is displayed on the touchscreen 131 may also be displayed on the display unit 120. In this case, a user may adjust the gain or the parameters on the touchscreen 131 while viewing changes in the ultrasound image, and may view the ultrasound image of the object in detail on the display unit 120.

The control panel 132 may be, but is not limited to, any one or more of a track ball and/or a hardware button, such as, for example, a mode selection button (e.g., an M, CW, PW, PD, C, 2D, 3D, or 4D mode), a probe button, and/or a power button.

The ultrasound apparatus 100 may include at least one probe connection unit 180. The ultrasound apparatus 100 may be configured to determine identification information which relates to a probe which is connected to the probe connection unit 180. For example, the ultrasound apparatus 100 may be configured to receive or read probe identification information which has previously been stored in the probe. In this specification, various types of probes may be used.

A method for providing an ultrasound image and/or a gain setup window for setting a gain which is implementable by using the ultrasound apparatus 100 will now be described in detail with reference to FIG. 2.

Figure 2:
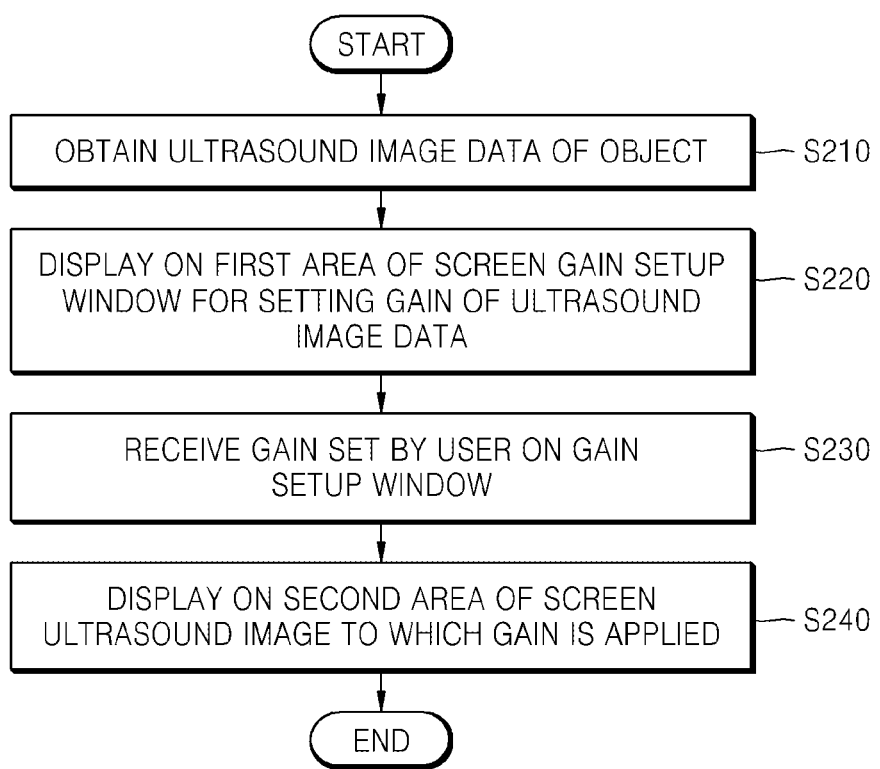
FIG. 2 is a flowchart which illustrates an information providing method which is executable by using an ultrasound apparatus, according to an exemplary embodiment.

FIG. 2 is a flowchart which illustrates an information providing method which is executable by using an ultrasound apparatus, according to an exemplary embodiment.

Referring to FIG. 2, the information providing method includes operations which are performable by using the ultrasound apparatus 100 illustrated in FIGS. 1A, 1B, and 1C. Accordingly, although not repeatedly provided, the descriptions provided above in relation to the ultrasound apparatus 100 may also be applied to the information providing method of FIG. 2.

In operation S210, the ultrasound apparatus 100 may obtain ultrasound image data which relates to an object. For example, the ultrasound apparatus 100 may transmit ultrasonic waves to the object and may generate the ultrasound image data based on an ultrasound echo signal which is received from the object.

In operation S220, the ultrasound apparatus 100 may display, on a first area of a screen, a gain setup window for setting a gain with respect to the ultrasound image data. The gain may include at least one of a time gain compensation (TGC) value and a lateral gain compensation (LGC) value.

The TGC value is a value which may be used to compensate for a reduction in intensity of an ultrasound signal based on a depth in a human body. The LGC value is a value which may be used to compensate for uneven respective differences in attenuation due to different corresponding transmission paths of ultrasonic beams. Hereinafter, for convenience of explanation, the TGC value is described as an example of the gain.

The ultrasound apparatus 100 may display, on the gain setup window, at least one slide bar for setting the gain. For example, the ultrasound apparatus 100 may align and display a plurality of slide bars on the gain setup window along a depth direction of an ultrasound image. The depth direction may refer to a direction in which a depth increases from the surface of an object to be diagnosed by using the ultrasound apparatus 100 with respect to interior soft tissues.

The slide bar refers to a GUI which is configured for enabling a user to adjust the gain at a certain depth.

The slide bars may be aligned in parallel at equal intervals along the depth direction.

When the ultrasound image data is obtained, if a gain which is set by the user does not exist, the ultrasound apparatus 100 may display, on the first area, an initial gain of the object based on the depth. In this case, the ultrasound apparatus 100 may display, on the screen, an ultrasound image which is generated by applying the initial gain.

In operation S230, the ultrasound apparatus 100 may receive the gain which is set by the user on the gain setup window. In particular, the ultrasound apparatus 100 may use the gain which is set by the user on the gain setup window.

The ultrasound apparatus 100 may sense a touch input of the user on the slide bar. The touch input may be any one or more of a drag input and/or a tap input. For example, the user may drag an adjustment button and/or tap a certain position on the slide bar.

"Drag" refers to an operation by which the user touches the screen by using a finger or a touch tool and then moves the finger or the touch tool to another position on the screen while continuously maintaining contact with the screen. "Tap" refers to an operation by which the user touches the screen by using a finger or a touch tool (e.g., an electronic pen or a stylus) and then lifts the finger or the touch tool from the screen without moving it with respect to the screen.

The ultrasound apparatus 100 may extract a gain which corresponds to a sensed position of the touch input. In particular, the ultrasound apparatus 100 may obtain the gain which is set by the user with respect to a depth represented by the slide bar.

According to another exemplary embodiment, the ultrasound apparatus 100 may sense a drag input of the user who performs the drag operation in the depth direction on the gain setup window (i.e., a direction which is perpendicular to the slide bars). The ultrasound apparatus 100 may extract individual gains which respectively correspond to depths of the ultrasound image based on positions of the drag input (e.g., coordinates of pixels where the drag input is sensed).

For example, if the user performs a drag operation on the gain setup window in a direction which is perpendicular to the slide bars along a straight line or a curved line, the ultrasound apparatus 100 may extract individual gains which respectively correspond to dragged positions and may set the gains with regard to the depths.

Based on the gains which are extracted based on the positions of the drag input, the ultrasound apparatus 100 may move and display adjustment buttons on the slide bars.

In operation S240, the ultrasound apparatus 100 may display, on a second area of the screen, an ultrasound image to which the gain set by the user on the gain setup window is applicable. For example, the ultrasound apparatus 100 may newly generate or partially change the ultrasound image of the object by applying the gain which is set by the user to the ultrasound image data.

Accordingly, the user may adjust the gain on the gain setup window while viewing the ultrasound image to which the adjusted gain is applied in real time. If the user sets a high gain, the ultrasound image may become brighter. If the user sets a low gain, the ultrasound image may become darker.

A method for receiving a set TGC value which is executable by using the ultrasound apparatus 100 will now be described in detail with reference to FIGS. 3, 4, 5, 6, and 7.

Figure 3:
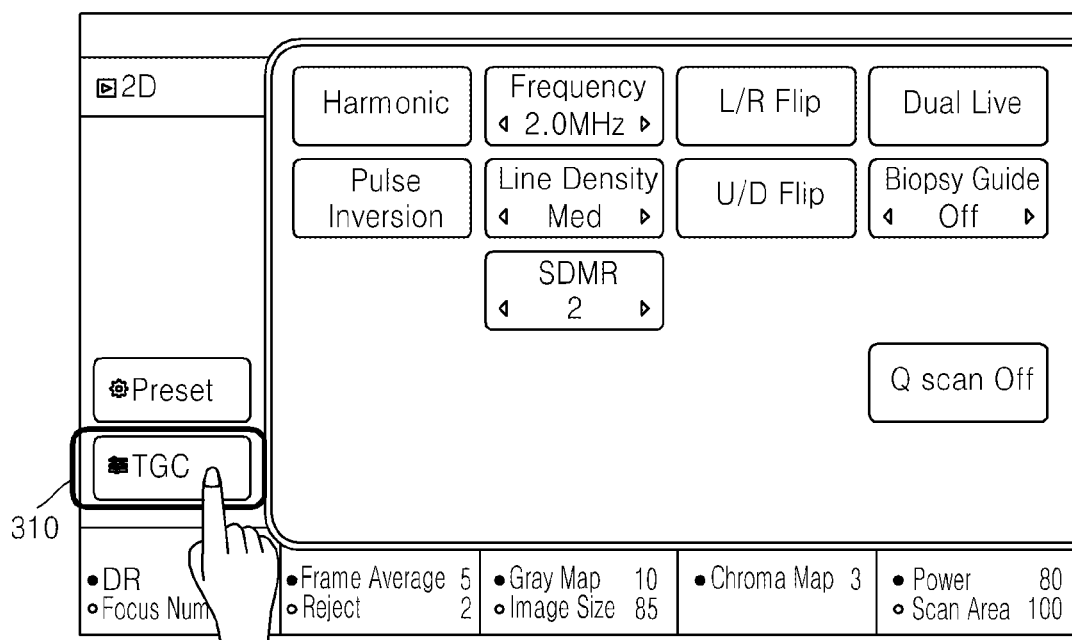
FIG. 3 is an image of a time gain compensation (TGC) setup screen of an ultrasound apparatus, according to an exemplary embodiment.

FIG. 3 is an image of a TGC setup screen 310 of the ultrasound apparatus 100, according to an exemplary embodiment.

As illustrated in FIG. 3, the ultrasound apparatus 100 may provide, on a touchscreen, the TGC setup button 310 which is used to be provided as a knob button. Accordingly, if a user touches the TGC setup button 310 on the touchscreen, the ultrasound apparatus 100 enters a TGC setup mode for enabling the user to set a TGC value.

FIG. 4 is an image of a gain setup window 410 for setting a gain, according to an exemplary embodiment.

As illustrated in FIG. 4, the ultrasound apparatus 100 may display, on a first area of a screen, the gain setup window 410 for setting a gain of ultrasound image data. In this case, the gain setup window 410 may include a plurality of slide bars for individually setting gains regarding a plurality of depths. The slide bars may be aligned in parallel in a depth direction.

The ultrasound apparatus 100 may display an ultrasound image 420 of an object on a second area of the screen. The ultrasound apparatus 100 may locate the second area where the ultrasound image 420 is displayed in relatively close proximity to the first area where the gain setup window 410 is displayed, and thus may prevent distributed attention when the user sets the TGC value.

Further, the ultrasound apparatus 100 may obtain a gain line 430 which corresponds to the gains which are set on the gain setup window 410, and may display the gain line 430 on the second area. A detailed description thereof will be provided below with reference to FIG. 6.

Figure 5A:
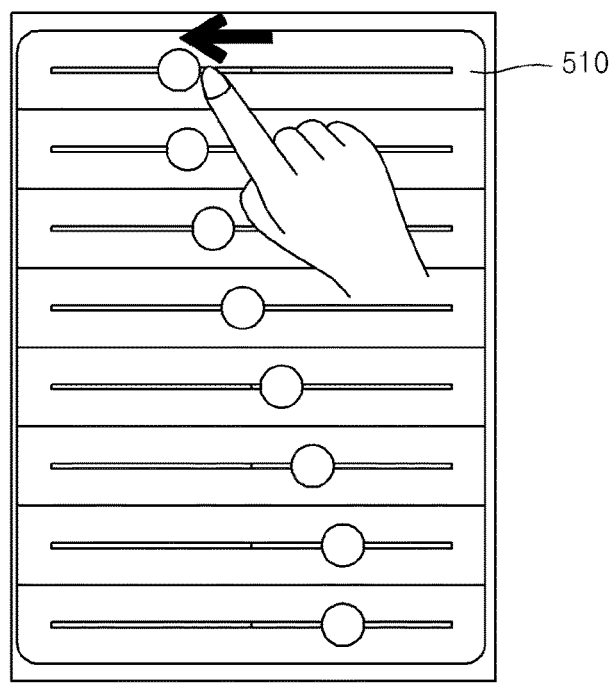
FIGS. 5A, 5B, and 5C are images which illustrate respective screens which relate to receiving a gain from a user, according to exemplary embodiments.
Figure 5B:
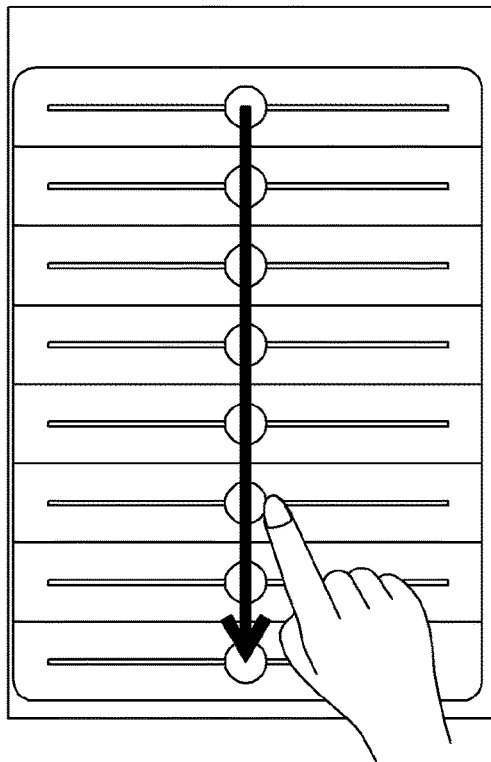
Figure 5C:
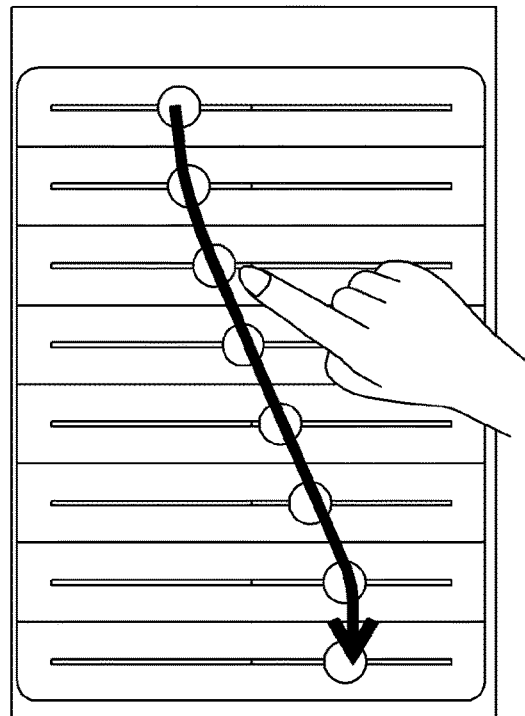

FIGS. 5A, 5B, and 5C are images which illustrate a screen for receiving a gain from a user, according to exemplary embodiments.

A user may set a TGC value by touching at least one slide bar and moving an adjustment button on the slide bar, or by performing a drag operation in a direction which is perpendicular to a plurality of slide bars.

As illustrated in FIG. 5A, a user may drag an adjustment button on a slide bar in a leftward direction or a rightward direction. In this case, the ultrasound apparatus 100 may sense the drag input of the user and may display the adjustment button at a position where the drag ends.

If the user drags an adjustment button on a first slide bar 510 in a leftward direction, a TGC value which corresponds to a depth which is represented by the first slide bar 510 may be reduced. In this case, a portion of an ultrasound image which corresponds to the depth represented by the first slide bar 510 may be reduced in brightness and thus may be displayed relatively dark.

A user may individually adjust respective TGC values which correspond to a plurality of depths by moving adjustment buttons on a plurality of slide bars which are allocated based on the depths.

As illustrated in FIGS. 5B and 5C, a user may simultaneously set TGC values which individually correspond to a plurality of depths by performing a drag operation on a gain setup window in the form of a straight line or a curved line. In this case, the ultrasound apparatus 100 may sense the drag input of the user and may move and display adjustment buttons on a plurality of slide bars to and on positions where the drag input is sensed.

Figure 6:
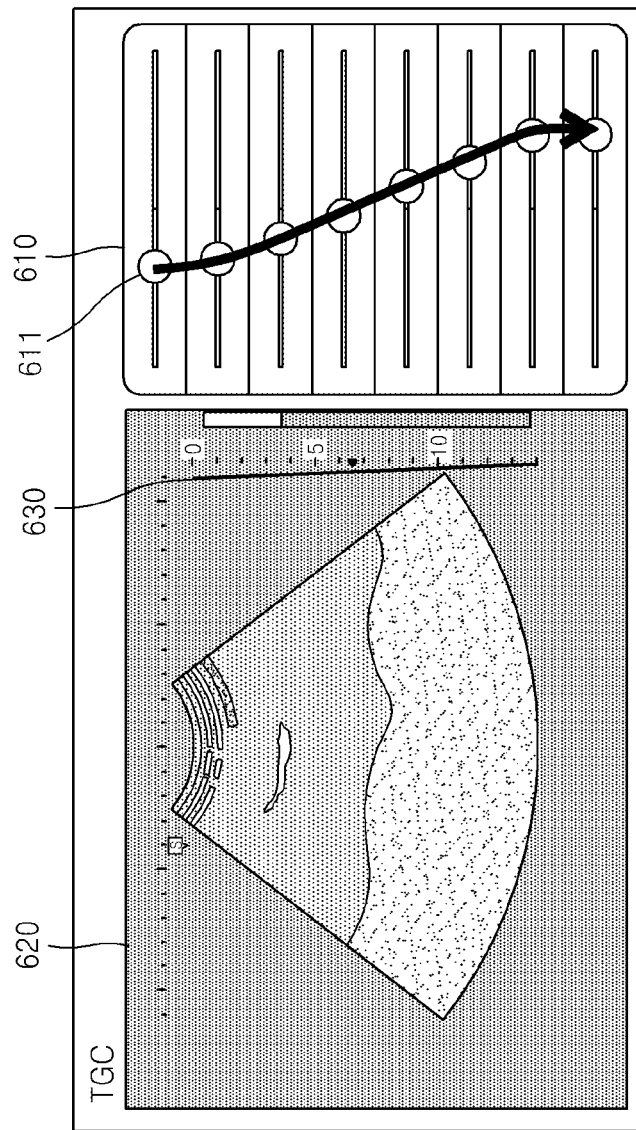
FIG. 6 is an image which illustrates a gain line which corresponds to gains, according to an exemplary embodiment.

FIG. 6 is an image which illustrates a gain line 630 which corresponds to gains, according to an exemplary embodiment.

The ultrasound apparatus 100 may obtain the gain line 630 which corresponds to gains which are set on a gain setup window 610, and may display the gain line 630 together with an ultrasound image 620.

For example, the ultrasound apparatus 100 may obtain the gain line 630 by connecting positions of adjustment buttons 611 on a plurality of slide bars (i.e., gains represented by the adjustment buttons 611). In this case, the ultrasound apparatus 100 may interpolate and calculate a gain between a first slide bar and a second slide bar by using a gain on the first slide bar and a gain on the second slide bar.

Further, if a user sets the gains by performing a drag operation on the gain setup window 610 in the form of a straight line or a curved line, the ultrasound apparatus 100 may obtain the gain line 630 based on corresponding dragged positions.

The ultrasound apparatus 100 may display the gain line 630 which corresponds to the gains which are set by the user on the gain setup window 610, adjacent to the ultrasound image 620 based on positions of depths of the ultrasound image 420, and thus may enable the user to intuitionally check, for example, a shape and/or a slope of the gain line 630.

Although FIG. 6 shows an example in which the gain line 630 is displayed on a right side of the ultrasound image 620, the gain line 630 is not limited thereto. In particular, the gain line 630 may be displayed on a bottom side, a top side, or a left side of the ultrasound image 620.

Figure 7:
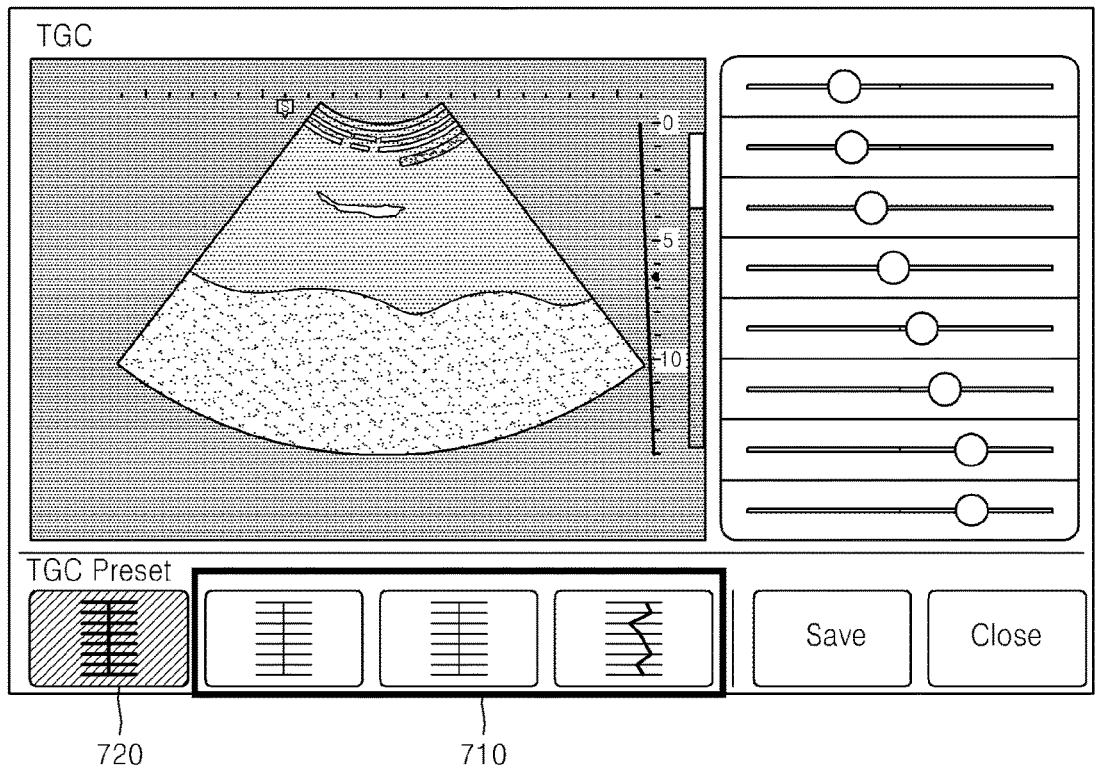
FIG. 7 is an image which illustrates a list of preset gains, according to an exemplary embodiment.

FIG. 7 is an image which illustrates a list 710 of preset gains, according to an exemplary embodiment.

As illustrated in FIG. 7, the ultrasound apparatus 100 may display the list 710 of one or more preset gains on a third area of a screen. The preset gain(s) may be previously set by a user or a system.

The list 710 of the preset gains may be displayed as images of gain lines which respectively correspond to the preset gains. In this case, the gain line may be variously displayed, for example, in the form of any one or more of a solid line, a dotted line, a dashed line, and/or a dotted and dashed line. The preset gain may be displayed in the form of an image which includes a plurality of slide bars.

The preset gains which are included in the list 710 may be automatically set by the ultrasound apparatus 100 or may be manually set by the user.

For example, the ultrasound apparatus 100 may extract and display typically and frequently used preset gains on the list 710, or may display preset gains selected by the user on the list 710.

The ultrasound apparatus 100 may extract a preset gain to be displayed on the third area of the screen based on at least one of probe setup information, application information, and object information. For example, if the user selects a 1D linear probe, the ultrasound apparatus 100 may extract a preset gain which is stored and mapped to the 1D linear probe and may display the extracted preset gain on the list 710. Further, if the user selects obstetrics (OB) from among a plurality of applications, the ultrasound apparatus 100 may extract a preset gain which relates to the application selected by the user and may display the extracted preset gain on the list 710.

The ultrasound apparatus 100 may further display at least one of a body marker, the application information, and the probe setup information on the list 710.

The application information refers to information which relates to a diagnosis department and/or a diagnosis site for ultrasound diagnosis. The diagnosis department may include any one or more of obstetrics (OB), gynecology (GYN), pediatrics (PD), chest surgery (CS), radiology (RD), neurosurgery (NS), abdomen, etc.

The body marker refers to a figure which represents a position or an object into which ultrasonic waves are scannable. Examples of the body marker may include any one or more of a liver shape, a heart shape, and a uterus shape. The probe setup information may refer to information which is set in relation to a probe which is configured for outputting an ultrasound signal. For example, when a low-frequency curved probe is used, 'low frequency convex' may be further displayed in addition to a corresponding preset gain. If a high-frequency linear probe is used, 'high frequency linear' may be further displayed in addition to a corresponding preset gain.

The ultrasound apparatus 100 may receive a selection of one preset gain on the list 710. The ultrasound apparatus 100 may display the selected preset gain on a gain setup window, and may display, on a second area of a screen, an ultrasound image to which the selected preset gain is applied. In this case, the ultrasound apparatus 100 may receive an additional setup from the user in relation to the selected preset gain. In particular, the user may adjust the gain which is displayed on the gain setup window in detail by entirely or partially adjusting the displayed gain.

The ultrasound apparatus 100 enables the user to easily set a TGC value by providing a few types of preset TGC values.

The ultrasound apparatus 100 may provide an initialization button 720 for initializing the gain which is set on the gain setup window. If a touch input on the initialization button 720 is sensed, the ultrasound apparatus 100 may display an initial gain on the gain setup window and may display, on the second area of the screen, an ultrasound image to which the initial gain is applied.

Figure 8:
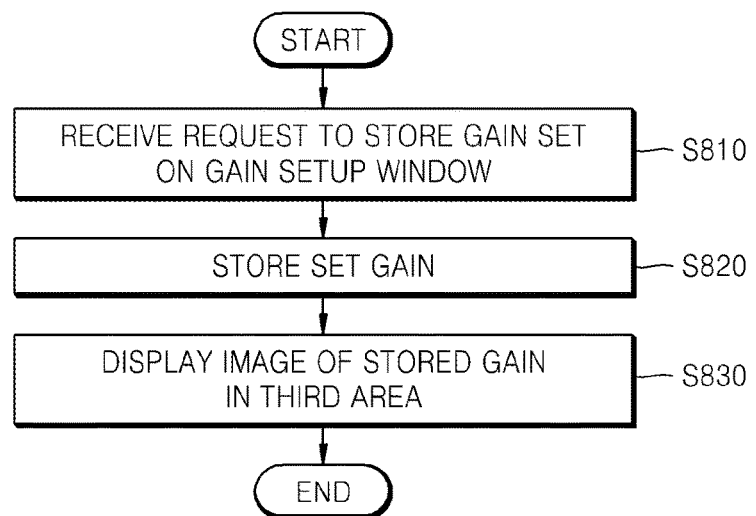
FIG. 8 is a flowchart which illustrates a gain storing method which is executable by using an ultrasound apparatus, according to an exemplary embodiment.

FIG. 8 is a flowchart which illustrates a gain storing method which is executable by using the ultrasound apparatus 100, according to an exemplary embodiment.

In operation S810, the ultrasound apparatus 100 may receive, from a user, a request to store a gain which is set on a gain setup window. The user may transmit such a request by touching a certain icon which is displayed on a screen or by selecting a physical button.

In operation S820, the ultrasound apparatus 100 may store, in the memory 160, the gain which is set on the gain setup window. The ultrasound apparatus 100 may store the gain which is set on the gain setup window by mapping the gain to at least one of probe setup information and application information. In addition, the ultrasound apparatus 100 may store the gain which is set on the gain setup window by connecting the gain to at least one parameter which has previously been set in relation to an ultrasound image. A detailed description thereof will be provided below.

In operation S830, the ultrasound apparatus 100 may display an image of the stored gain in a third area. For example, if the user selects a save button, the ultrasound apparatus 100 may store, in the memory 160, a gain which is currently displayed on the gain setup window, and may display the gain which is currently displayed on the gain setup window on a list of preset gains. A detailed description thereof will be provided below with reference to FIG. 9.

Figure 9A:
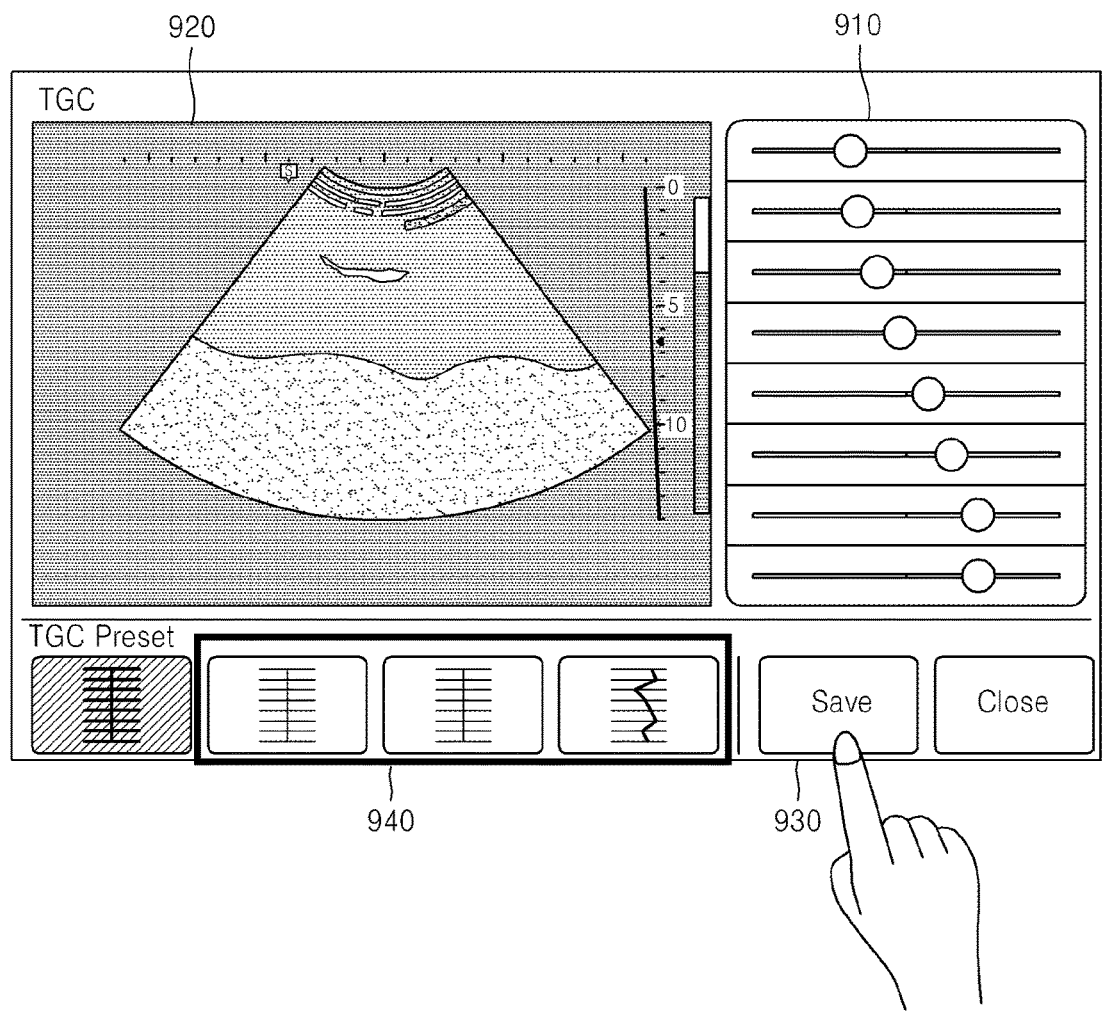
FIGS. 9A, 9B, and 9C are images which illustrate a graphic user interface (GUI) for storing a gain, according to an exemplary embodiment.
Figure 9B:
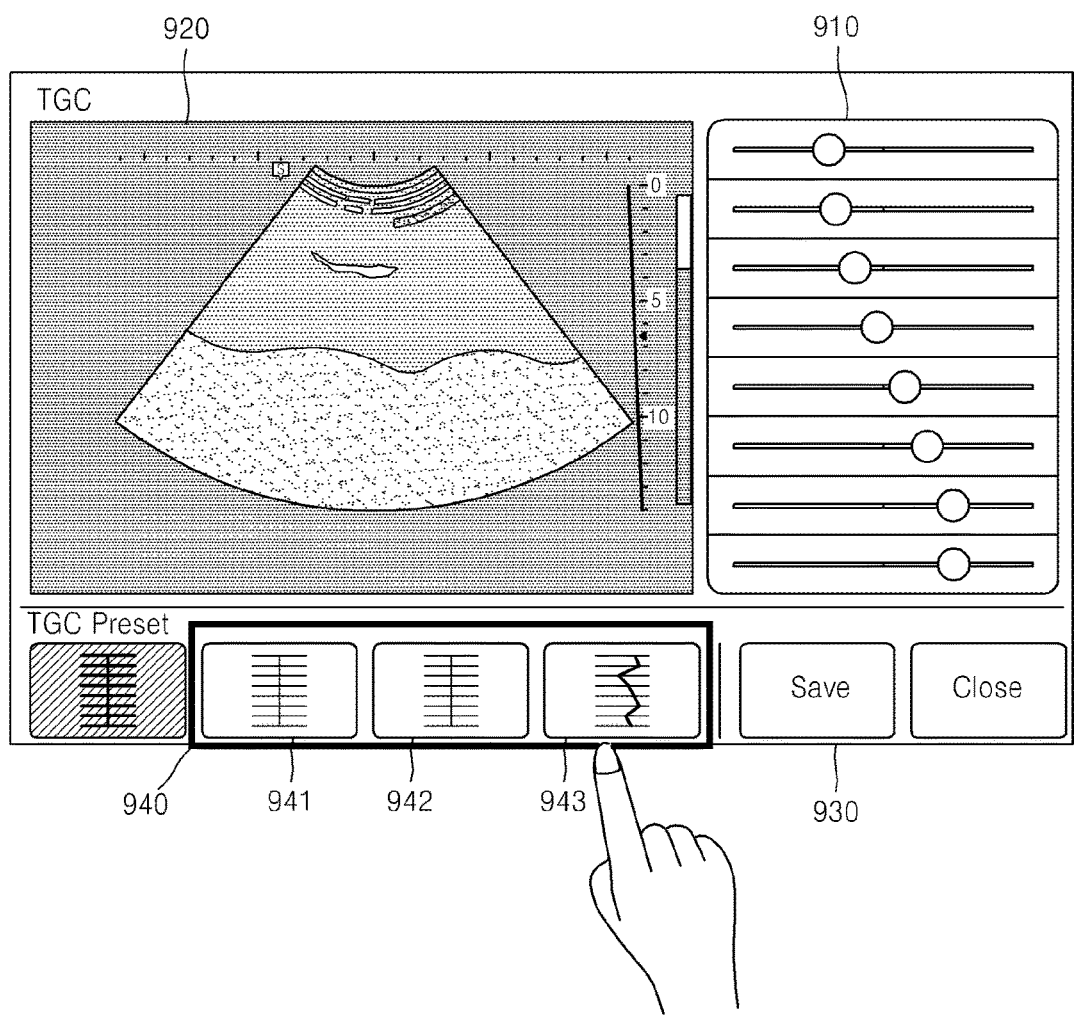
Figure 9C:
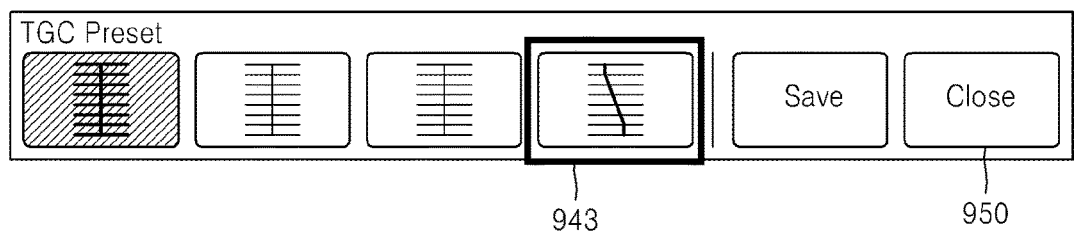

FIGS. 9A, 9B, and 9C are images which illustrate a GUI which is configured for storing a gain, according to an exemplary embodiment.

As illustrated in FIG. 9A, the ultrasound apparatus 100 may output a save button 930 on a touchscreen. In this case, the ultrasound apparatus 100 may sense a touch input of a user on the save button 930. In this case, the ultrasound apparatus 100 enters a save mode.

As illustrated in FIG. 9B, when operating in the save mode, the ultrasound apparatus 100 may identifiably display an area (or a slot) for displaying a gain which is currently displayed on a gain setup window 910 on a list 940 of preset gains. For example, the ultrasound apparatus 100 may display a yellow frame around buttons 941, 942, and 943 for displaying images of the preset gains.

If a selection of the third button 943 is received from the user, as illustrated in FIG. 9C, the ultrasound apparatus 100 may store, in the memory 160, the gain which is currently displayed on the gain setup window 910, and may display, on the third button 943, an image of the gain which is currently displayed on the gain setup window 910.

Although FIG. 9C shows an example in which the image of the third button 943 is changed, according to an exemplary embodiment, the ultrasound apparatus 100 may newly generate a button for displaying the gain which is currently displayed on the gain setup window 910 and may further display the newly generated button next to the third button 943.

Accordingly, because the ultrasound apparatus 100 may display, on a certain button, a gain curve which corresponds to a current TGC value, the user may intuitionally check the stored TGC value (or a TGC line).

The ultrasound apparatus 100 may provide, on the touch screen, a close button 950 for closing a TGC setup mode. If a touch input of the user on the close button 950 is sensed, the ultrasound apparatus 100 may close the TGC setup mode.

According to another exemplary embodiment, if a touch input of the user is not sensed for a predetermined period of time, the ultrasound apparatus 100 may automatically close the TGC setup mode.

Figure 10:
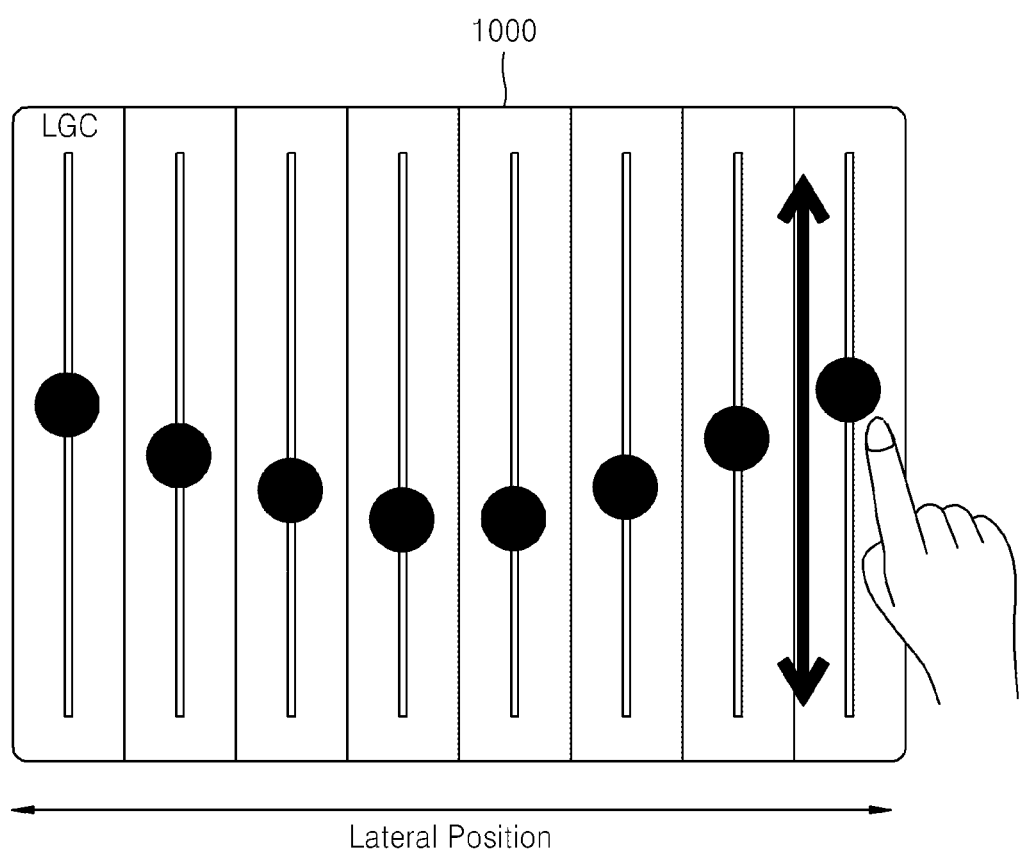
FIG. 10 is an image which illustrates a gain setup window for setting a lateral gain compensation (LGC) value, according to an exemplary embodiment.

FIG. 10 is an image which illustrates a gain setup window for setting an LGC value, according to an exemplary embodiment.

Although a TGC value is described above as an example of a gain, the descriptions of the TGC value with respect to FIGS. 3 through 9 may also be applied to the LGC value.

As illustrated in FIG. 10, the ultrasound apparatus 100 may provide an LGC setup window on a touchscreen. For example, the ultrasound apparatus 100 may align a plurality of slide bars for setting LGC values in parallel in the LGC setup window.

In this case, a user may individually set each respective one of the LGC values by adjusting each of the slide bars, or may simultaneously set the LGC values by performing a drag operation in a direction which is perpendicular to the slide bars (a lateral direction) in the form of a straight line or a curved line.

The ultrasound apparatus 100 may display, on a screen in real time, an ultrasound image to which the LGC values set by the user are applied. In addition, the ultrasound apparatus 100 may store, in the memory 160, the LGC values which are set by the user, and may display a list of preset LGC values on the screen. A detailed description thereof is similar to the above description of the TGC value and thus is not provided here. Although the TGC setup window and the LGC setup window are displayed separately, the ultrasound apparatus 100 may also display the TGC setup window and the LGC setup window on the same screen.

Figure 11:
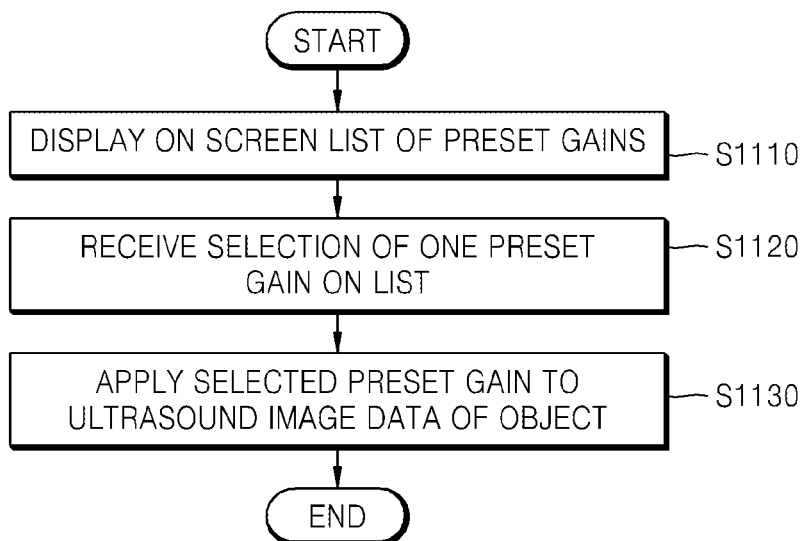
FIG. 11 is a flowchart which illustrates an information providing method which is executable by using an ultrasound apparatus, according to another exemplary embodiment.

FIG. 11 is a flowchart which illustrates an information providing method which is executable by using the ultrasound apparatus 100, according to another exemplary embodiment.

In operation S1110, the ultrasound apparatus 100 may display, on a screen, a list of preset gains. The list of the preset gains may be displayed as images of gain lines, or as numbers or text which represent the preset gains. A detailed description of the list of the preset gains is the same as the above description in relation to FIG. 7 and thus is not provided here.

The ultrasound apparatus 100 may extract one or more preset gains from the memory 160 or from a personalized server (e.g., a cloud server) and may form a list of the extracted preset gains. In particular, the ultrasound apparatus 100 may obtain a list of preset gains from any one or more of an external storage medium and/or an internal storage medium.

According to another exemplary embodiment, the ultrasound apparatus 100 may receive a list of preset gains from an external apparatus via wired and/or wireless communications.

In operation S1120, the ultrasound apparatus 100 may receive a selection of one preset gain which is included in the list. For example, the ultrasound apparatus 100 may sense a touch input (e.g., a tap gesture, a swipe gesture, or a flick gesture) or a voice command of a user in relation to one preset gain.

In operation S1130, the ultrasound apparatus 100 may apply the selected preset gain to ultrasound image data of an object. The ultrasound apparatus 100 may display, on the screen, an ultrasound image to which the selected preset gain is applied.

The ultrasound apparatus 100 may display, on a gain setup window, the preset gain which is selected by the user. For example, the ultrasound apparatus 100 may move at least one slide bar which is displayed on the gain setup window, based on the selected preset gain.

The ultrasound apparatus 100 may receive an additional setup from the user in relation to the preset gain which is displayed on the gain setup window. For example, the user may adjust the preset gain which is displayed on the gain setup window in detail by adjusting the slide bar which is displayed on the gain setup window.

The ultrasound apparatus 100 may store the gain which is additionally set by the user. In this case, the ultrasound apparatus 100 may store the gain which is additionally set by the user in at least one of an internal storage medium and/or an external storage medium (e.g., a universal serial bus (USB) memory or an optical disk).

In this case, the ultrasound apparatus 100 may further display, on the list of the preset gains, the gain which is stored in the internal storage medium and/or the external storage medium.

The ultrasound apparatus 100 may transmit the preset gain and/or the list of the preset gains to an external apparatus via wired and/or wireless communications. The external apparatus may be, but is not limited to, any one or more of a device of the user (e.g., a mobile phone, a smart phone, a laptop computer, a tablet PC, or an electric book device), another ultrasound apparatus, and/or a personalized server (e.g., a cloud server).

Figure 12:
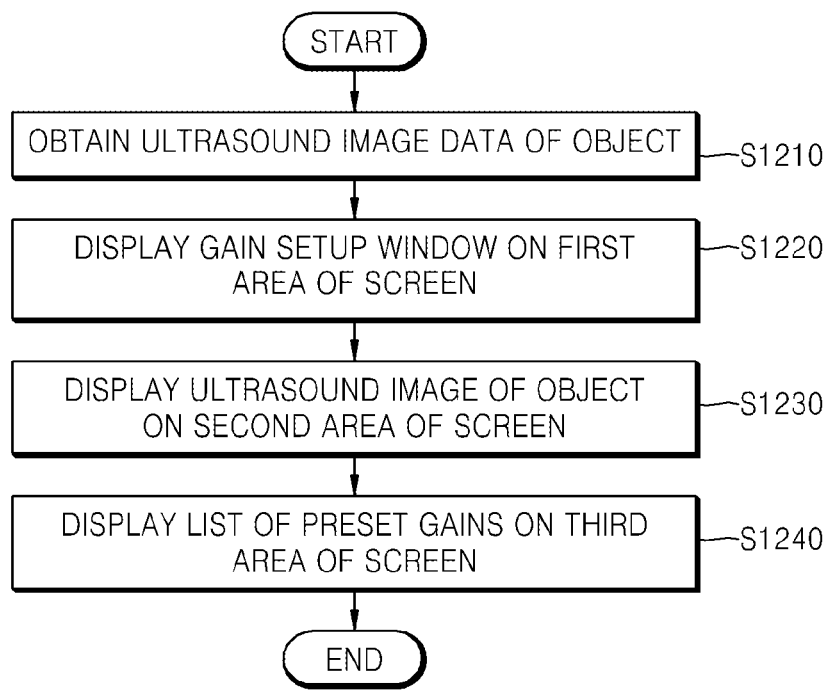
FIG. 12 is a flowchart which illustrates an information providing method which is executable by using an ultrasound apparatus, according to another exemplary embodiment.

FIG. 12 is a flowchart which illustrates an information providing method which is executable by using the ultrasound apparatus 100, according to another exemplary embodiment.

In operation S1210, the ultrasound apparatus 100 may obtain ultrasound image data which relates to an object.

In operation S1220, the ultrasound apparatus 100 may display, on a first area of a screen, a gain setup window for setting a gain of the obtained ultrasound image data.

In operation S1230, the ultrasound apparatus 100 may display an ultrasound image of the object on a second area of the screen based on the obtained ultrasound image data.

In operation S1240, the ultrasound apparatus 100 may display a list of preset gains on a third area of the screen. The ultrasound apparatus 100 may obtain the list of the preset gains from an external storage medium.

The ultrasound apparatus 100 may receive a selection of one preset gain from among the preset gains included in the list. The ultrasound apparatus 100 may display the selected preset gain on the gain setup window, and may display, on the second area of the screen, an ultrasound image to which the selected preset gain is applied.

For example, as illustrated in FIG. 9A, the ultrasound apparatus 100 may display the gain setup window 910, an ultrasound image 920, and the list 940 of the preset gains on one screen. In this case, a user may set a TGC value and/or an LGC value by directly adjusting slide bars which are displayed on the gain setup window 910, or may select one preset gain (e.g., item 943 of FIG. 9B) from among the preset gains which are displayed on the list 940.

If the user selects one preset gain (e.g., item 943) from among the preset gains which are displayed on the list 940, the ultrasound apparatus 100 may display the selected preset gain (e.g., item 943) on the gain setup window 910. The ultrasound apparatus 100 may receive an additional setup from the user in relation to the preset gain which is displayed on the gain setup window 910. The ultrasound apparatus 100 may store, in the memory 160 and/or in an external storage medium, the gain which is additionally set on the gain setup window 910, and may display an image of the stored gain on the list 940 of the preset gains.

The ultrasound apparatus 100 may display at least one parameter which is mapped to the selected preset gain (e.g., item 943). According to another exemplary embodiment, the ultrasound apparatus 100 may determine at least one parameter which is mapped to the selected preset gain (e.g., item 943) and may apply the determined parameter to a system.

In particular, the ultrasound apparatus 100 may change the setup of an ultrasound system based on at least one parameter which is mapped to the selected preset gain (e.g., item 943). A detailed description thereof will be provided below with reference to FIGS. 13, 14, 15, 16, and 17.

FIG. 13 is a table which shows setup parameters which relate to an ultrasound image, according to an exemplary embodiment.

As illustrated in FIG. 13, the setup parameters which relate to the ultrasound image may include at least one of frequency 1305, dynamic range 1310, frame average 1315, reject level 1320, gray map 1325, spatial compound 1330, dynamic magnetic resonance (DMR+) 1335, harmonic 1340, scan area 1345, edge enhance 1350, speed 1355, power 1360, line density 1365, full spectrum image (FSI) 1370, focus number 1375, gain 1380, and depth 1385.

The frequency 1305 refers to a parameter which relates to changing a transmission or reception frequency which is applied to a probe. For example, a user may set the frequency 1305 by selecting one of Pen, Gen, and Res.

The dynamic range 1310 is a parameter which relates to adjusting brightness by changing a ratio of a minimum value and a maximum value of an input signal. For example, the user may set the dynamic range 1310 by selecting a value between 50 and 200.

The frame average 1315 is a parameter which relates to reducing random noise of the ultrasound image. For example, the user may set the frame average 1315 by selecting a value between 0 and 15.

The reject level 1320 is a parameter which relates to reducing noise of the ultrasound image. For example, the user may set the reject level 1320 by selecting a value between 1 and 32.

The gray map 1325 is a parameter which relates to determining a gray scale by changing a post curve of the ultrasound image. For example, the user may set the gray map 1325 by selecting a value between 1 and 13. A detailed description thereof will be provided below with reference to FIG. 16.

The spatial compound 1330 is a parameter which relates to adjusting a density of the ultrasound image. For example, the user may set the spatial compound 1330 by selecting one of low, medium, and high.

The DMR+ 1335 is a parameter which relates to post-processing of the ultrasound image and is a parameter which relates to reducing noise and enhancing edges. For example, the user may set the DMR+ 1335 by selecting a value between 1 and 5.

The harmonic 1340 is a parameter which relates to optimizing the ultrasound image by using a high frequency. For example, the user may set the harmonic 1340 by selecting one of on and off.

The scan area 1345 is a parameter which relates to adjusting a horizontal width (%) of the ultrasound image. For example, the user may set the scan area 1345 by selecting a value between 40 and 100.

The edge enhance 1350 is a parameter which relates to sharpening edges of images of tissues or organs. For example, the user may set the edge enhance 1350 by selecting a value between −3 and 3.

The speed 1355 is a parameter which relates to increasing a resolution by adjusting a speed of tissues. For example, the user may set the speed 1355 by selecting a value between 1440 and 1620 m/s.

The power 1360 is a parameter which relates to selecting an intensity of an ultrasonic output. For example, the user may set the power 1360 by selecting a value between 10 and 100.

The line density 1365 is a parameter which relates to adjusting a density of the ultrasound image. For example, the user may set the line density 1365 by selecting one of low, mid1, mid2, and high.

The FSI 1370 is a parameter which relates to adjusting a ratio of mixing frequencies. For example, the user may set the FSI 1370 by selecting a value between 1 and 3.

The focus number 1375 is a parameter which relates to setting positions and a number of focuses. For example, the user may set the focus number 1375 by selecting a value between 1 and 4.

The gain 1380 is a parameter which relates to adjusting a brightness of the ultrasound image. For example, the user may set the gain 1380 by selecting a value between 1 and 100.

The depth 1385 is a parameter which relates to adjusting a depth of the ultrasound image to be scanned. The depth 1385 may vary based on the type of a probe which is used with respect to the image. For example, with respect to a convex probe, the user may set the depth 1385 by selecting a value between 6 and 30 cm.

Figure 14A:
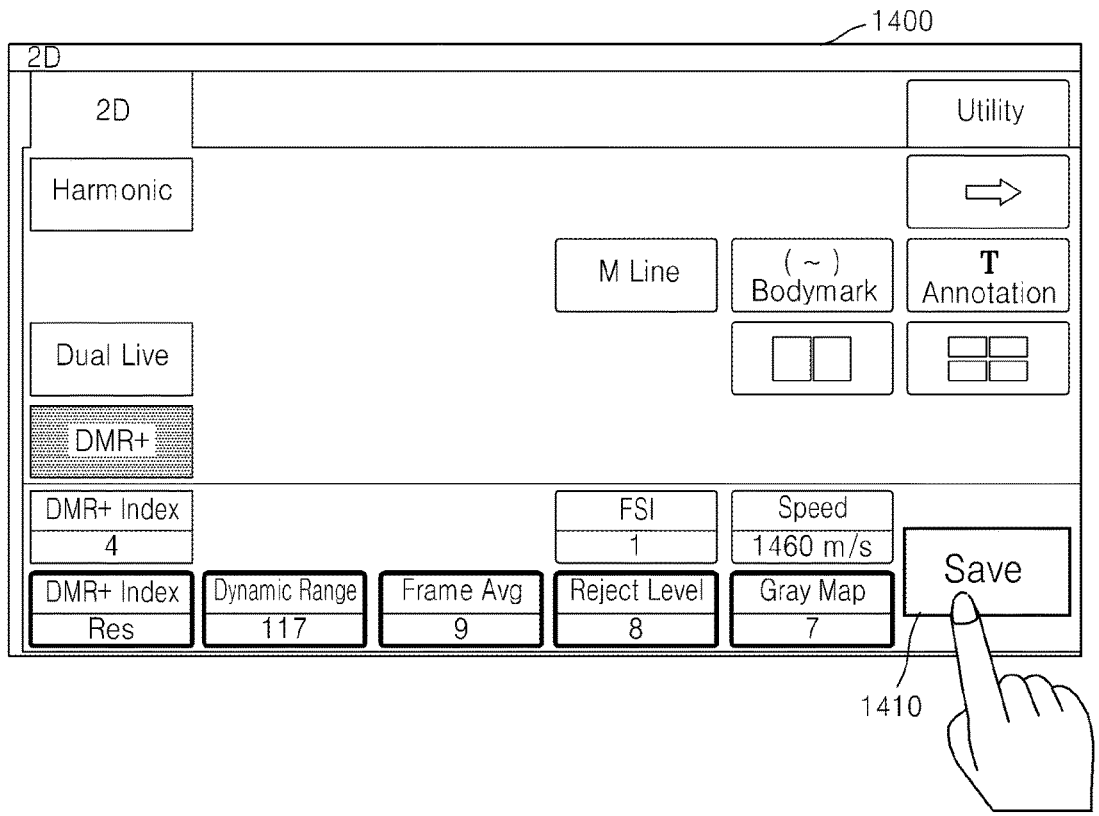
FIGS. 14A and 14B are images which illustrate a GUI for setting parameters which relate to an ultrasound image, according to an exemplary embodiment.
Figure 14B:
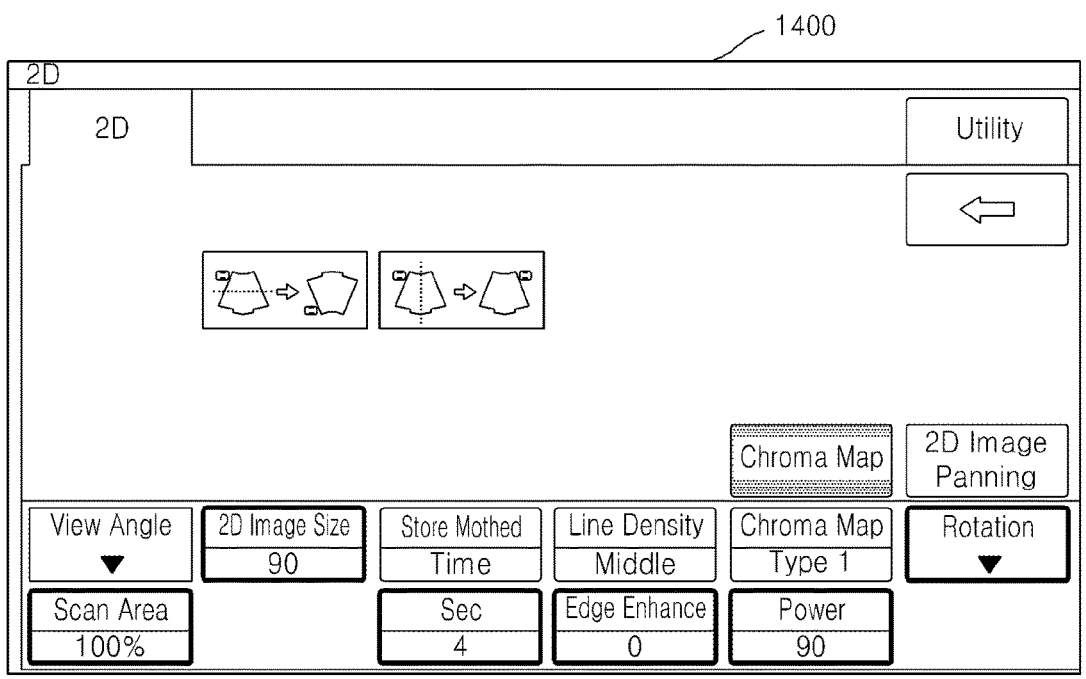

FIGS. 14A and 14B are images which illustrate a GUI which is configured for setting parameters which relate to an ultrasound image, according to an exemplary embodiment.

The ultrasound apparatus 100 may provide a setup window 1400 which is configured for enabling a user to individually set the parameters which relate to the ultrasound image.

For example, as illustrated in FIG. 14A, the ultrasound apparatus 100 may provide, on a screen, the setup window 1400 for setting parameters such as the frequency 1305, the dynamic range 1310, the frame average 1315, the reject level 1320, the gray map 1325, the DMR+ 1335, the harmonic 1340, the speed 1355, and the FSI 1370.

Further, as illustrated in FIG. 14B, the ultrasound apparatus 100 may provide the setup window 1400 for setting parameters such as the scan area 1345, the edge enhance 1350, the power 1360, and the line density 1365.

The ultrasound apparatus 100 may sense a parameter which is input (or selected) by a user on the setup window 1400. The ultrasound apparatus 100 may store the input (or selected) parameter in response to a request of the user to store the parameter. A detailed description thereof will be provided below with reference to FIG. 15.

FIGS. 15A, 15B, 15C, and 15D are images which illustrate a GUI which is configured for enabling a user to store at least one preset parameter, according to an exemplary embodiment.

Figure 15A:
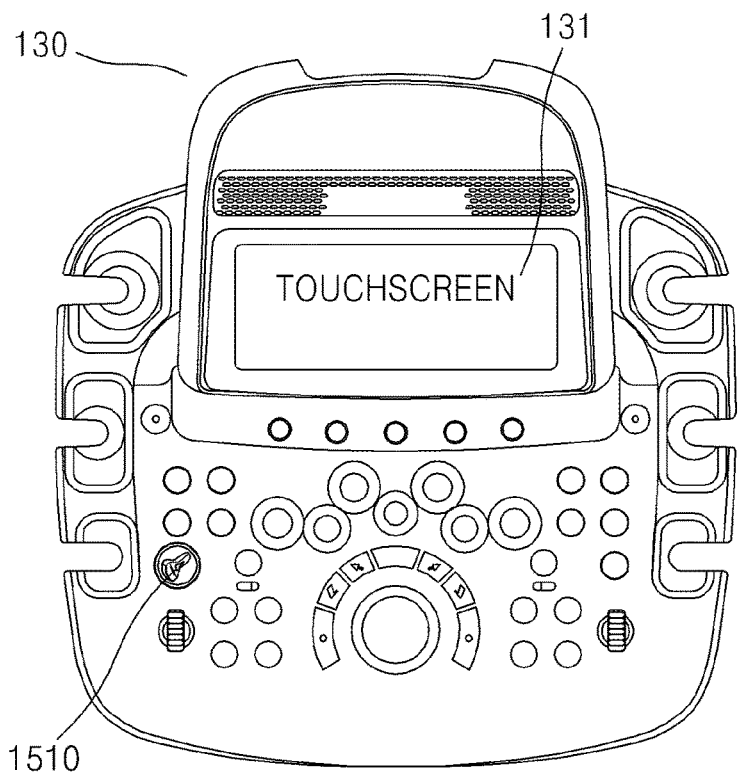
FIGS. 15A, 15B, 15C, and 15D are images which illustrate a GUI for storing at least one preset parameter, according to an exemplary embodiment.
Figure 15B:
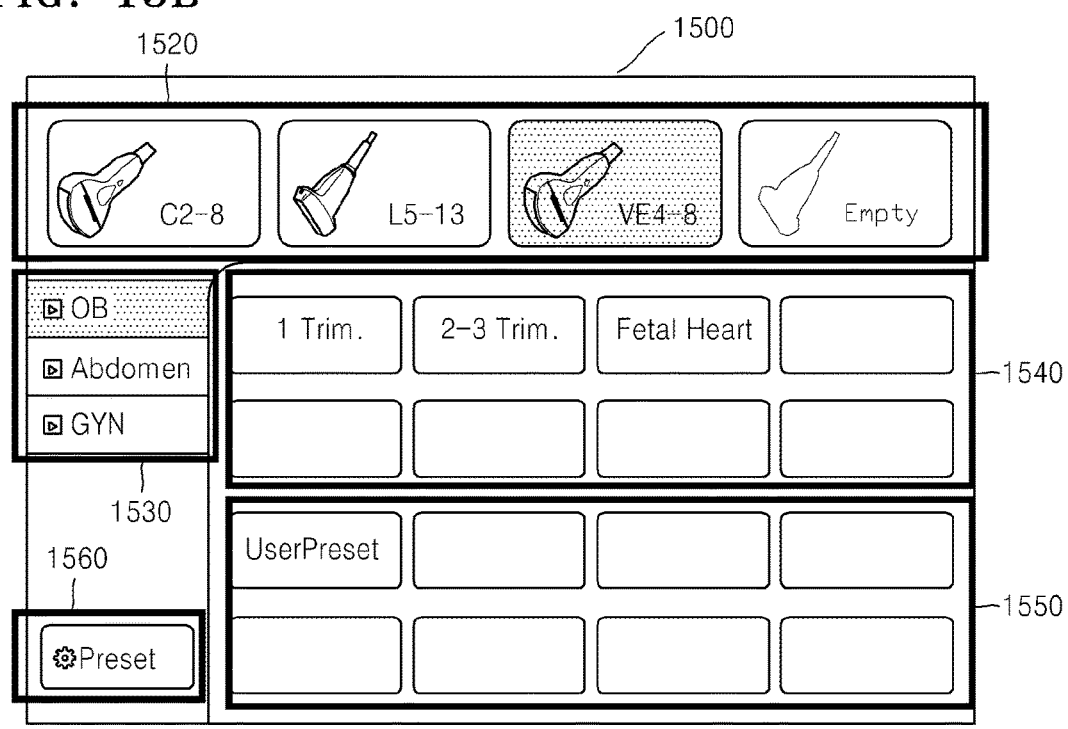

As illustrated in FIG. 15A and FIG. 15B, if a user touches a certain icon on the touchscreen 131 or selects a certain button on the control panel 132, the ultrasound apparatus 100 may provide a GUI 1500 for storing a parameter which is set by the user.

For example, if a selection of a probe button 1510 by the user is sensed, the ultrasound apparatus 100 may provide, on the touchscreen 131, the GUI 1500 for adjusting a gain or at least one parameter which relates to an ultrasound image.

As illustrated in FIG. 15B, the ultrasound apparatus 100 may display, on a predetermined area of the GUI 1500, a probe list 1520 which includes identification information which relates to one or more probes which are connected to the ultrasound apparatus 100. For example, if a probe 1 C2-8, a probe 2 L5-13, and a probe 3 VE4-8 are connected to the ultrasound apparatus 100, the ultrasound apparatus 100 may display identification information which relates to each of the probe 1 C2-8, the probe 2 L5-13, and the probe 3 VE4-8 on the probe list 1520. Identification information which relates to a probe is information which may be used for identifying the probe and may include, for example, any one or more of a probe image, a probe name, and a probe type.

The ultrasound apparatus 100 may sense a selection of at least one probe from the probe list 1520 by the user. For example, the user may select the probe 3 VE4-8 from the probe list 1520.

In addition, the ultrasound apparatus 100 may display a list 1530 of applications (e.g., diagnosis departments) on the predetermined area of the GUI 1500 and may receive a selection of an application from the list 1530 by the user. For example, the user may select "Abdomen" from the list 1530 of the applications.

In this case, the ultrasound apparatus 100 may display a list of presets which correspond to the probe 3 VE4-8 which is selected by the user. Further, according to another exemplary embodiment, the ultrasound apparatus 100 may display a list of presets which correspond to the probe 3 VE4-8 and the application (e.g., "Abdomen") which are selected by the user. In this case, the list of the presets may include system presets which include parameters which are previously set by a system and are unchangeable, and user presets which include parameters which are arbitrarily set by the user.

The ultrasound apparatus 100 may provide, on the GUI 1500, a default area 1540 for displaying the system presets which are mapped to the parameters which are previously set by the system and are unchangeable, and an arbitrary area 1550 for displaying the user presets which are mapped to the parameters which are arbitrarily set by the user.

If the user selects one preset item (e.g., "fetal heart") from the list of the presets which respectively correspond to at least one of the probe and the application and then touches a predetermined button 1560, the ultrasound apparatus 100 may provide preset parameters which correspond to the selected preset item (i.e., "fetal heart").

Figure 15C:
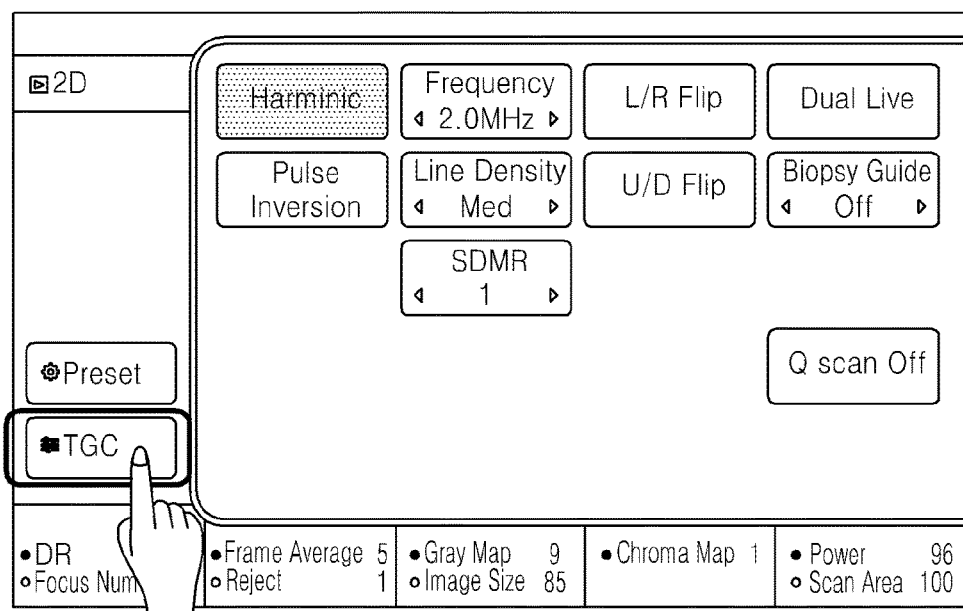

For example, as illustrated in FIG. 15C, the ultrasound apparatus 100 may display preset parameters which respectively correspond to each of the frequency 1305, the frame average 1315, the gray map 1325, the harmonic 1340, the line density 1365, and the focus number 1375 which are mapped to the selected preset item (i.e., "fetal heart"). In this case, the user may generate a new user preset by changing the parameters which are displayed on a screen. The newly generated user preset may be displayed on the arbitrary area 1550. In this case, the user may set a name of the newly generated user preset.

For example, a first user may generate a user preset named 'user1' and may store a plurality of parameters which are set by the first user by mapping the parameters to 'user1'. In addition, a second user may store a plurality of parameters which are set by the second user by mapping these parameters to a user preset named 'user2'. If a third user sets parameters in relation to a face of a fetus (i.e., a different selected preset item), the third user may store the parameters which are set in relation to the face of the fetus by mapping these parameters to a user preset named 'Face'.

Further, the user may set a gain and may generate a new user preset by adding the set gain. For example, if the user touches a TGC button on the screen, the ultrasound apparatus 100 may provide a setup window for setting the gain (e.g., a TGC value).

Figure 15D:
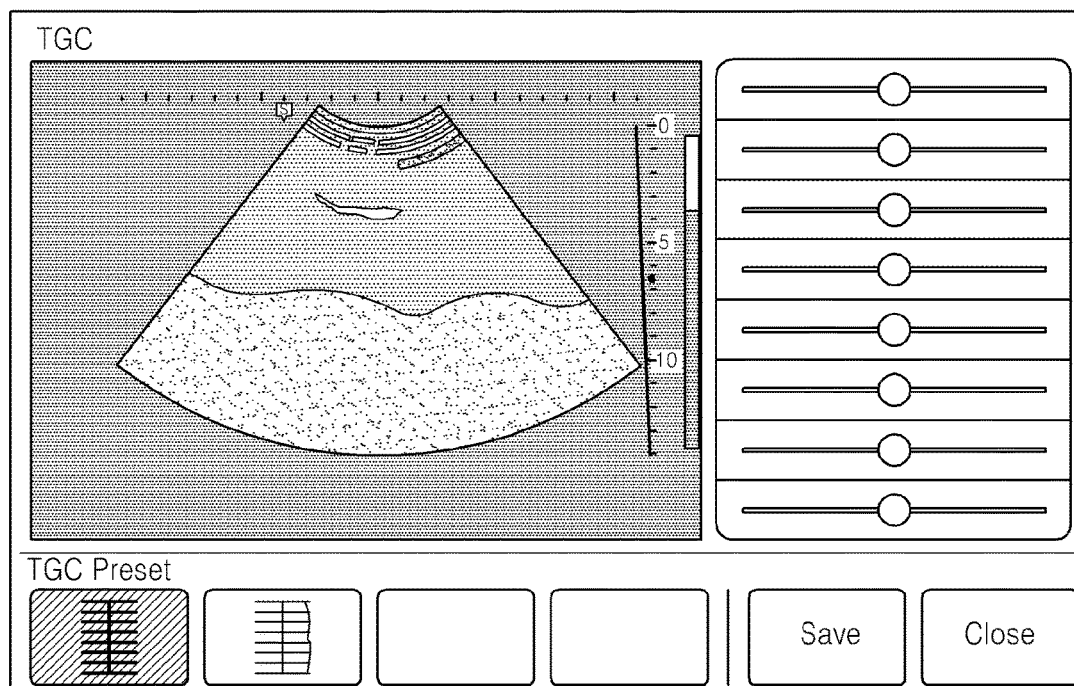

As illustrated in FIG. 15D, the ultrasound apparatus 100 may provide a gain setup window and may receive a gain which is set by the user on the gain setup window. A method thereof is described in detail above and thus is not described here.

If the ultrasound apparatus 100 receives, from the user, a request to store the set gain, the ultrasound apparatus 100 may generate a user preset which includes the set gain. In this case, the gain which is set by the user may be mapped to at least one of a probe (e.g., the probe 3) and application information (e.g., Abdomen) which are selected by the user and may be stored as a user preset. The gain which is set by the user may be stored as a user preset in the arbitrary area 1560 together with preset parameters. Accordingly, the ultrasound apparatus 100 enables the user to make a frequently-used TGC line for each probe and to store the TGC line as a user preset. For example, the user may store a TGC line which is frequently used for a carotid ultrasound image by mapping this TGC line to a probe which is used for generating the carotid ultrasound image. In this case, the ultrasound apparatus 100 may generate a preset mapping table which includes the identification information which relates to the probes, the parameters which relate to the ultrasound image, and the gains, which are mapped to each other, and may store the preset mapping table in the memory 160.

Although FIGS. 15A, 15B, 15C, and 15D show an example when a probe and an application are selected first and then a parameter is adjusted or a TGC value is set, according to an exemplary embodiment, the parameter or the TGC value may be set first and then the probe or the application may be selected and connected to the set parameter or the TGC value.

A method for automatically extracting a gain which is stored and mapped to a probe and applying the gain to a system by the ultrasound apparatus 100 will now be described.

Figure 16:
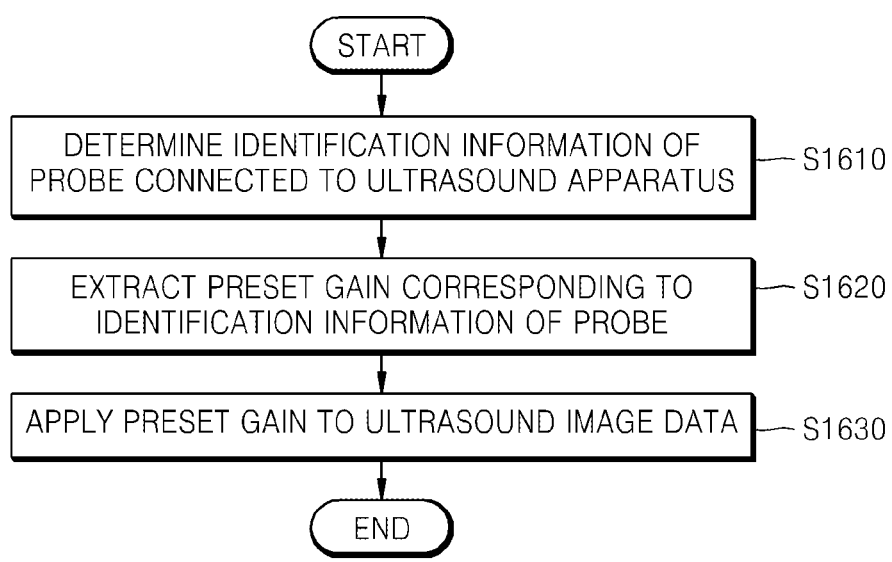
FIG. 16 is a flowchart which illustrates an information providing method which is executable by using an ultrasound apparatus and which method is based on identification information which relates to a probe, according to an exemplary embodiment.

FIG. 16 is a flowchart which illustrates an information providing method which is executable by using the ultrasound apparatus 100 based on identification information of a probe, according to an exemplary embodiment.

In operation S1610, the ultrasound apparatus 100 may determine identification information which relates to a probe which is connected to the ultrasound apparatus 100. For example, the ultrasound apparatus 100 may determine identification information which relates to a probe which is connected to the ultrasound apparatus 100, for example, a probe image, a probe name, and a probe type, by receiving the identification information which relates to the connected probe which is stored in the memory 160.

If a plurality of probes are connected to the ultrasound apparatus 100, the ultrasound apparatus 100 may determine identification information which relates to each of the probes and may display a probe list which includes the identification information which relates to each of the probes.

In operation S1620, the ultrasound apparatus 100 may extract a preset gain which corresponds to the identification information which relates to the probe. For example, the ultrasound apparatus 100 may extract, from a preset mapping table, a preset gain which is mapped to the identification information which relates the probe based on the identification information which relates to the probe.

The ultrasound apparatus 100 may receive a selection of identification information which relates to one probe on the probe list, which probe list includes the identification information which relates to each of the probes which are connected to the ultrasound apparatus 100. In this case, the ultrasound apparatus 100 may extract a preset gain which corresponds to the identification information which relates to the selected probe.

The ultrasound apparatus 100 may extract a plurality of preset gains which correspond to the identification information which relates to the probe. In this case, the ultrasound apparatus 100 may display a list of the preset gains on a screen. In this case, the ultrasound apparatus 100 may receive a selection of one preset gain from the list of the preset gains.

The preset gains which correspond to the identification information which relates to the probe may be individually included in a plurality of user presets. In particular, a preset gain may be stored as a user preset together with other parameters. In this case, the ultrasound apparatus 100 may display a list of user presets which correspond to the identification information which relates to the probe and may receive a selection of one user preset from the list of the user presets.

The ultrasound apparatus 100 may receive application information which represents a diagnosis department. For example, the application information may include, is not limited to, obstetrics (OB), gynecology (GYN), pediatrics (PD), chest surgery (CS), radiology (RD), neurosurgery (NS), abdomen, etc.

The ultrasound apparatus 100 may extract a preset gain which corresponds to the identification information which relates to the probe and the application information which are selected by a user.

In operation S1630, the ultrasound apparatus 100 may apply the preset gain to ultrasound image data.

For example, if the ultrasound apparatus 100 obtains ultrasound image data which relates to an object by using a probe which is selected by the user, the ultrasound apparatus 100 may apply a preset gain which corresponds to the probe selected by the user to the ultrasound image data. In particular, the ultrasound apparatus 100 may automatically extract a gain which is stored and mapped to a probe and may apply the extracted gain to a system.

The ultrasound apparatus 100 may display, on a predetermined area of the screen, the preset gain which corresponds to the identification information which relates to the probe which is connected to the ultrasound apparatus 100.

If a plurality of probes are connected to the ultrasound apparatus 100, the ultrasound apparatus 100 may display, on the screen, the preset gain which corresponds to the identification information which relates to the probe which is selected by the user from among the probes. In this case, the ultrasound apparatus 100 may receive an additional setup from the user in relation to the preset gain which is displayed on the screen. In particular, the user may determine the preset gain which is mapped to the selected probe and may adjust the preset gain in detail.

A case in which a gain and various parameters are stored as a user preset which corresponds to identification information which relates to a probe will now be described with reference to FIGS. 17A, 17B, 18A, and 18B.

FIGS. 17A and 17B and 18A and 18B are images which show a parameter and a gain which correspond to a user preset which is selected by a user, according to an exemplary embodiment.

Figure 17A:
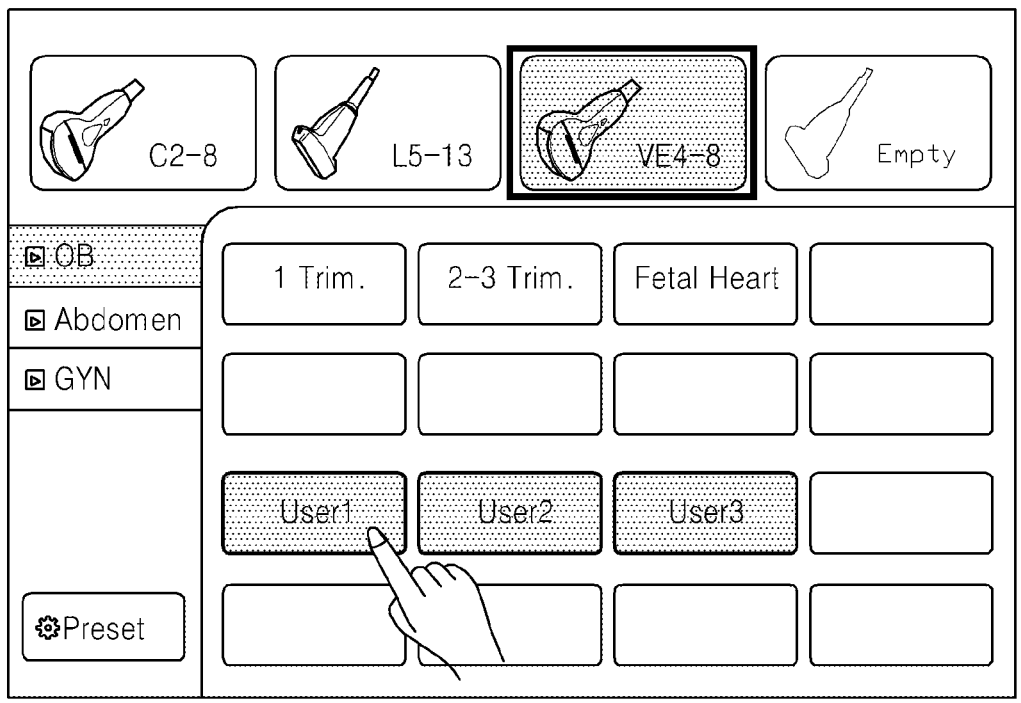
FIGS. 17A, 17B, 18A, and 18B are images which show a parameter and a gain which correspond to a user preset which is selected by a user, according to an exemplary embodiment.

The ultrasound apparatus 100 may display a preset list which corresponds to identification information which relates to a selected probe and application information. In this case, the preset list may include at least one user preset which includes at least one parameter and a gain which have previously been set in relation to an ultrasound image. As illustrated in FIG. 17A, if a user selects 'user1' from the preset list, the ultrasound apparatus 100 may apply preset parameters and a gain which are mapped to 'user1' to a system, or may display these preset parameters and gain on a screen.

Figure 17B:
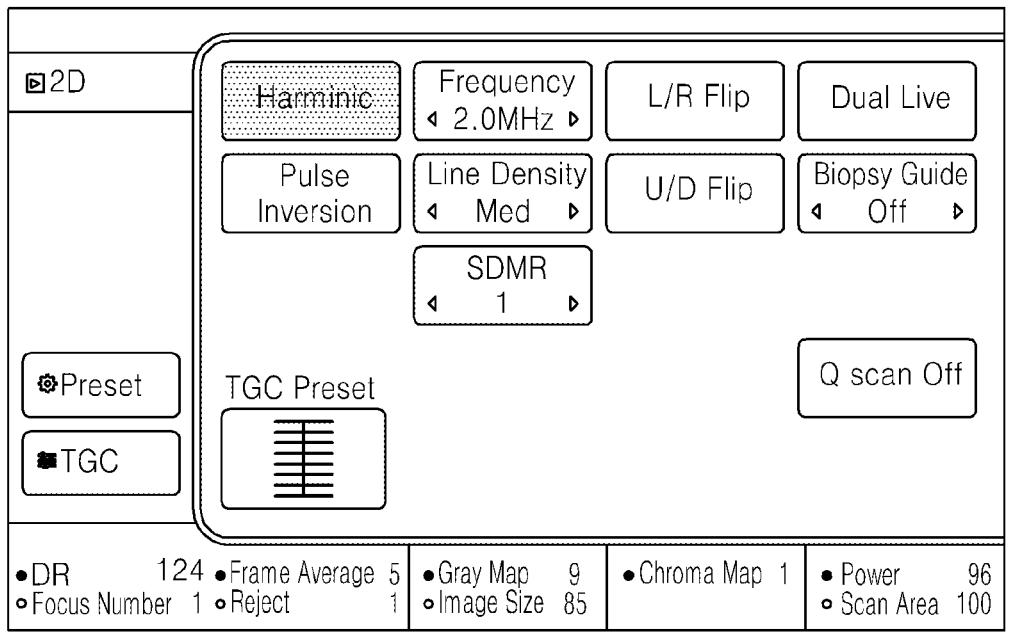

For example, as illustrated in FIG. 17B, the ultrasound apparatus 100 may display parameters (for example, DMR+: on, Frequency: Res, Dynamic Range: 117, Frame Average: 5, Reject Level: 1, Gray Map: 9, Line Density: Med, Power: 96, Scan Area: 100, and Focus Number: 1) and a TGC line which are mapped to 'user1'.

Figure 18A:
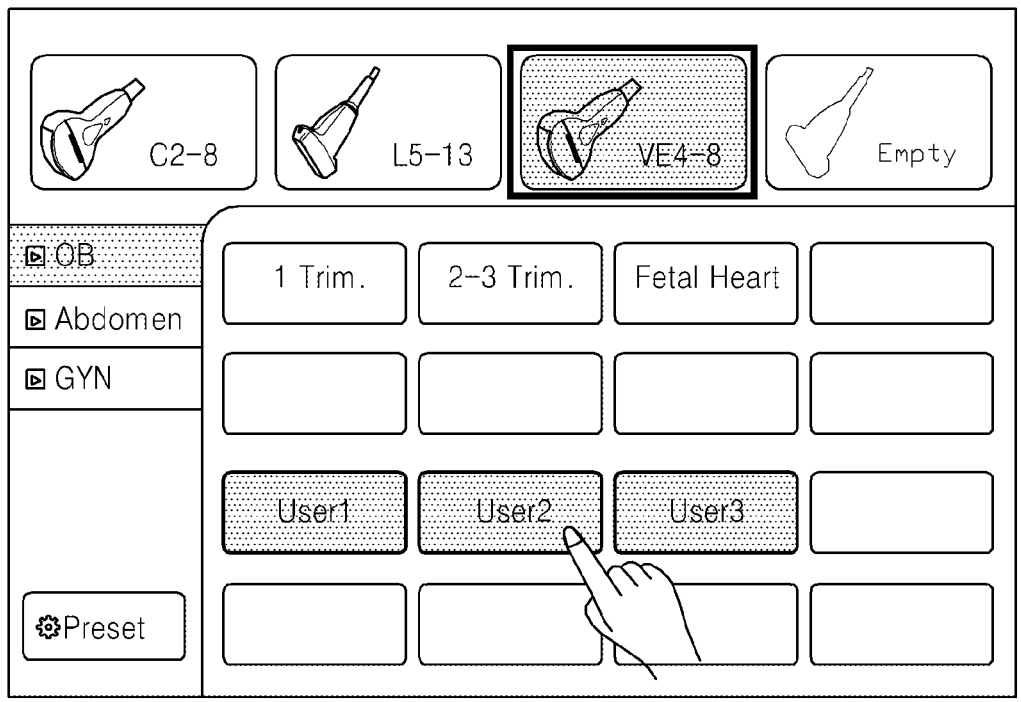

As illustrated in FIG. 18A, if a user selects 'user2' from the preset list, the ultrasound apparatus 100 may apply preset parameters and a gain which are mapped to 'user2' to a system, or may display these preset parameters and gain on a screen.

Figure 18B:
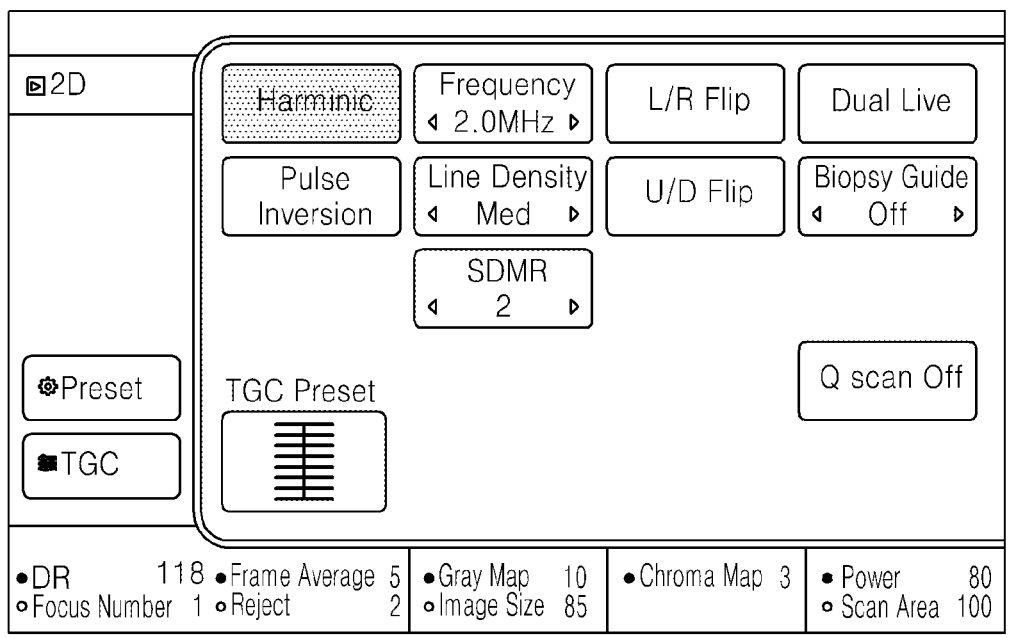

For example, as illustrated in FIG. 18B, the ultrasound apparatus 100 may display parameters (for example, DMR+: on, Frequency: Pen, Dynamic Range: 120, Frame Average: 10, Reject Level: 2, Gray Map: 10, Chroma Map: 3, Power: 80, and Scan Area: 100) and a TGC line which are mapped to 'user2'.

In this case, the user may edit (for example, delete, add, and/or change) the parameters and the TGC line which are included in the user preset. In addition, the user may change a name of the user preset. For example, the user may change 'user1' into 'face'.

The ultrasound apparatus 100 may display a detailed list which relates to at least one parameter from among the parameters which have previously been set in relation to the ultrasound image. For example, the ultrasound apparatus 100 may provide a list of gray maps which list is usable for determining a gray scale or a list of curves which list is usable for selecting a predetermined area of 3D volume data. A detailed description thereof will be provided below with reference to FIGS. 19A, 19B, 20A, and 20B.

Figure 19A:
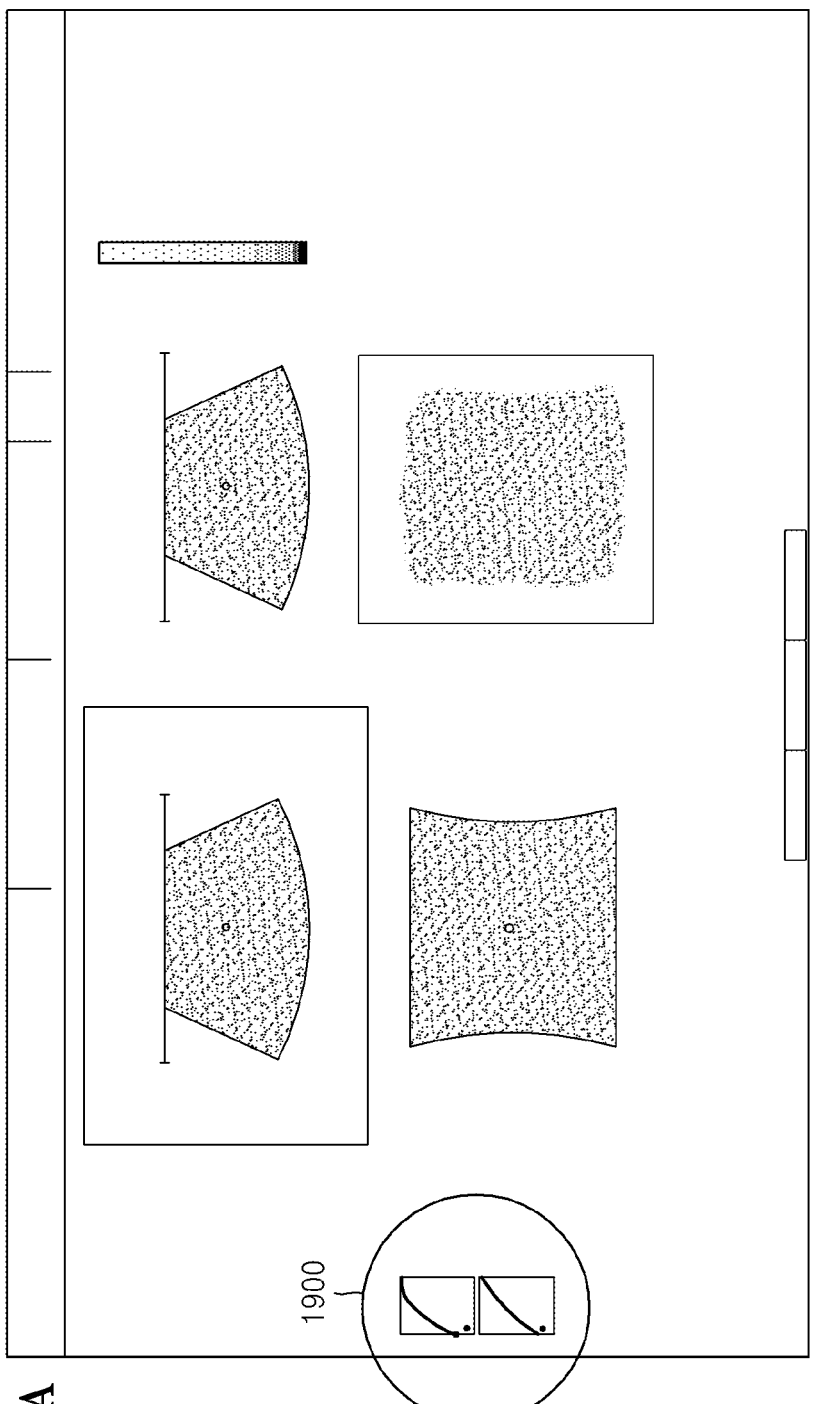
FIGS. 19A and 19B are images which show a list of preset gray maps, according to an exemplary embodiment.
Figure 19B:
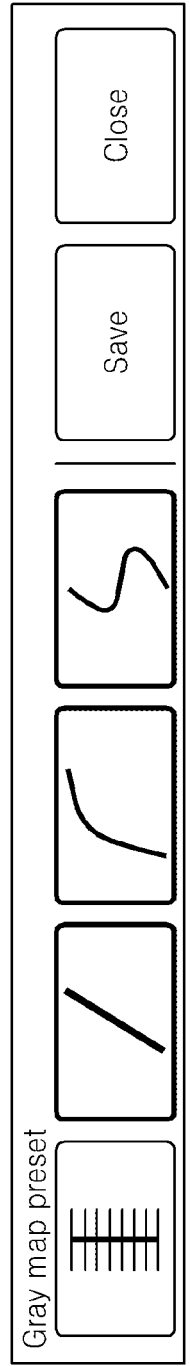

FIGS. 19A and 19B are images which illustrate a list of preset gray maps, according to an exemplary embodiment.

As illustrated in FIG. 19A, a user may adjust a shape of a gray map 1900 which is usable for determining a gray scale. For example, the user may variously set the shape of the gray map 1900 in the form of any one or more of a straight line, a parabola, and/or an S-shaved curve. If the user requests, the ultrasound apparatus 100 may store a gray map which is set by the user. The gray map may include a 2D image gray map and/or a 3D image gray map.

As illustrated in FIG. 19B, the ultrasound apparatus 100 may display a list of preset gray maps on a screen. The list of the preset gray maps may be displayed in the form of images of lines, numbers, and/or text.

The ultrasound apparatus 100 may extract one or more preset gray maps from the memory 160 or a personalized server (e.g., a cloud server), and may form a list of the extracted preset gray maps. In particular, the ultrasound apparatus 100 may obtain a list of preset gray maps from an external storage medium or an internal storage medium.

According to another exemplary embodiment, the ultrasound apparatus 100 may receive a list of preset gray maps from an external apparatus via wired and/or wireless communications.

The ultrasound apparatus 100 may receive a selection of one preset gray map from the list of the preset gray maps. For example, the ultrasound apparatus 100 may sense a touch input (e.g., a tap gesture, a swipe gesture, or a flick gesture) or a voice command of a user in relation to one preset gray map. In this case, the ultrasound apparatus 100 may apply the selected preset gray map to ultrasound image data which relates to an object.

The ultrasound apparatus 100 may display the selected gray map on the screen and may receive an additional setup from the user in relation to the selected gray map. In particular, the user may adjust the selected gray map in detail.

Figure 20A:
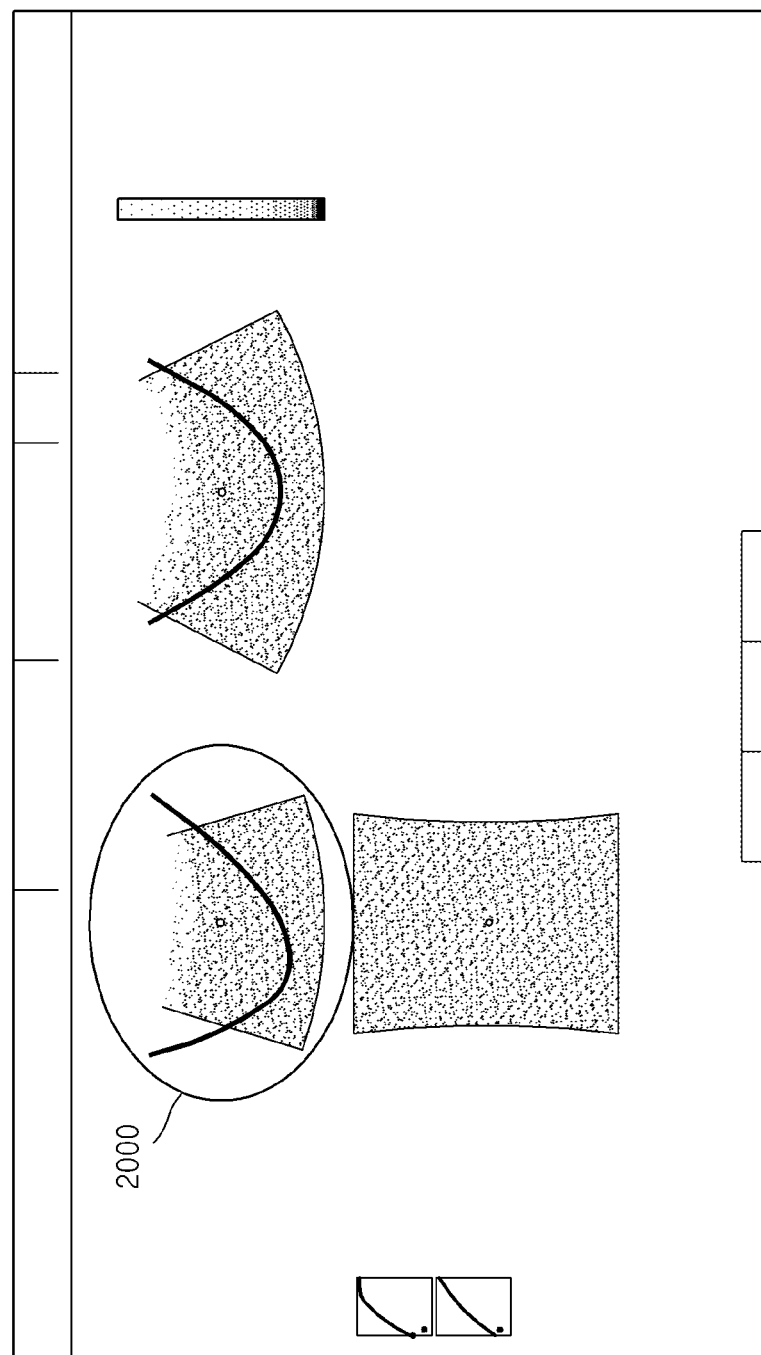
FIGS. 20A and 20B are images which show a list of preset curves, according to an exemplary embodiment.
Figure 20B:
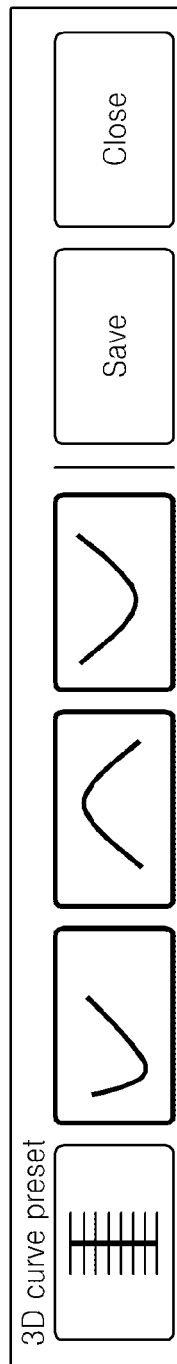

FIGS. 20A and 20B are images which illustrate a list of preset curves, according to an exemplary embodiment.

As illustrated in FIG. 20A, a user may adjust a shape of a curve 2000 which is usable for selecting a predetermined area of 3D volume data. The curve 2000 may have any one or more of various shapes. If the user requests, the ultrasound apparatus 100 may store a curve which is set by the user.

As illustrated in FIG. 20B, the ultrasound apparatus 100 may display a list of preset curves on a screen. The list of the preset curves may be displayed as images. The ultrasound apparatus 100 may extract one or more preset curves from the memory 160 or a personalized server (e.g., a cloud server), and may form a list of the extracted preset curves. According to another exemplary embodiment, the ultrasound apparatus 100 may receive a list of preset curves from an external apparatus via wired and/or wireless communications.

The ultrasound apparatus 100 may further display, for example, an application type (e.g., OB) and a body marker (e.g., a face of a fetus) which relate to a curve on the list of the preset curves.

The ultrasound apparatus 100 may receive a selection of one curve from the list of the preset curves. In this case, the ultrasound apparatus 100 may apply the selected curve to ultrasound image data which relates to an object.

The ultrasound apparatus 100 may provide a list of various parameters which relate to an ultrasound image in addition to a gain (e.g., a TGC value or an LGC value), and thus may enable a user to easily set the parameters which relate to the ultrasound image.

One or more of the above-described exemplary embodiments may be implemented with at least one processor and includes a transitory and/or non-transitory computer readable medium including program instructions for executing various operations realized by a computer. The computer readable medium may include program instructions, a data file, and a data structure, separately or cooperatively. The program instructions and the media may be those specially designed and constructed for the purposes of one or more of the exemplary embodiments, or they may be of the kind well known and available to one of ordinary skill in the art of computer software arts. Examples of the computer readable media include magnetic media (e.g., hard disks, floppy disks, and magnetic tapes), optical media (e.g., CD-ROMs or DVD), magneto-optical media (e.g., floptical disks), and hardware devices (e.g., ROMs, RAMs, or flash memories, etc.) that are specially configured to store and perform program instructions. The media may also be transmission media, such as, for example, optical or metallic lines, wave guides, etc. which specify the program instructions, data structures, etc. Examples of the program instructions include both machine code, such as produced by a compiler, and files which contain codes which relate to high-level languages that may be executed by the computer using an interpreter.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

What is claimed is:

1. An ultrasound apparatus comprising:
a touch screen;
at least one memory storing instructions; and
at least one processor that executes the instructions to cause the ultrasound apparatus to:
in response to receiving an input to enter a mode which initializes time gain compensation (TGC) values, enter the mode which initializes TGC values and display, on the touch screen, a graphical user interface (GUI) for setting TGC values, the GUI displaying initialized positions along depths for indicating initialized TGC values along the depths,
obtain an ultrasound image by applying the initialized TGC values to at least one ultrasound echo signal reflected from an object and detected by a probe,
display the obtained ultrasound image,
receive, from a user, a single drag input within the GUI displaying initialized positions along depths,
in response to the received single drag input, change a plurality of the displayed initialized positions to thereby change the initialized TGC values indicated by the plurality of displayed positions to adjusted TGC values,
display a line with the ultrasound image, the line indicative of a position of the single drag input within the GUI in correspondence with a depth of the ultrasound image, and
obtain an ultrasound image by applying the adjusted TGC values to the at least one ultrasound echo signal.

2. The ultrasound apparatus of claim 1, wherein the line is displayed at a side of the ultrasound image, based on information about locations on the ultrasound image, which correspond to depths represented by points of the line.

3. The ultrasound apparatus of claim 1, wherein the line is displayed at a side of the ultrasound image so that depths represented by points of the line match with depths represented by points on the ultrasound image.

4. The ultrasound apparatus of claim 1, wherein
the touch screen displays an initialization element, and
the received input to enter the mode which initializes TCG values is a selection of the initialization element by the user.

5. A method comprising:
by an ultrasound apparatus:
in response to receiving an input to enter a mode which initializes time gain compensation (TGC) values, entering the mode which initializes TGC values and displaying, on a touch screen of the ultrasound apparatus, a graphical user interface (GUI) for setting TGC values, the GUI displaying initialized positions along depths for indicating initialized TGC values along the depths,
obtaining an ultrasound image by applying the initialized TGC values to at least one ultrasound echo signal reflected from an object and detected by a probe,
displaying the obtained ultrasound image,
receiving, from a user, a single drag input within the GUI displaying initialized positions along depths,
in response to the received single drag input, changing a plurality of the displayed initialized positions to thereby change the initialized TGC values indicated by the plurality of displayed positions to adjusted TGC values, display a line with the ultrasound image, the line indicative of a position of the single drag input within the GUI in correspondence with a depth of the ultrasound image, and obtaining an ultrasound image by applying the adjusted TGC values to the at least one echo signal.

6. The method of claim 5, wherein the line is displayed at a side of the ultrasound image, based on information about locations on the ultrasound image, which correspond to depths represented by points of the line.

7. The method of claim 5, wherein the line is displayed at a side of the ultrasound image so that depths represented by points of the line match with depths represented by points on the ultrasound image.

8. The method of claim 5, wherein the line is displayed at a side of the ultrasound image so that a peak point of the line matches with an uppermost portion of the ultrasound image and a lowest point of the line matches with a lowermost portion of the ultrasound image.

9. The method of claim 5, further comprising:

by the ultrasound apparatus:

displaying an initialization element on the touch screen, wherein the received input to enter the mode which initializes TCG values is a selection of the initialization element by the user.

* * * * *